(12) United States Patent
    Fink

(10) Patent No.: US 11,766,182 B2
(45) Date of Patent: Sep. 26, 2023

(54) SYSTEMS AND METHODS FOR REAL-TIME SIGNAL PROCESSING AND FITTING

(71) Applicant: The Arizona Board of Regents on Behalf of the University of Arizona, Tucson, AZ (US)

(72) Inventor: Wolfgang Fink, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 375 days.

(21) Appl. No.: 15/174,993

(22) Filed: Jun. 6, 2016

(65) Prior Publication Data

US 2016/0353996 A1     Dec. 8, 2016

Related U.S. Application Data

(60) Provisional application No. 62/171,895, filed on Jun. 5, 2015.

(51) Int. Cl.
   *A61B 5/0205*   (2006.01)
   *A61B 5/00*     (2006.01)
   (Continued)

(52) U.S. Cl.
   CPC ........ *A61B 5/02055* (2013.01); *A61B 5/0002* (2013.01); *A61B 5/259* (2021.01);
   (Continued)

(58) Field of Classification Search
   CPC ........ A61B 5/04012; A61B 2560/0223; A61B 5/0022; A61B 5/6814; A61B 5/7282; A61B 5/7275; A61B 5/4064; A61B 2576/026; A61B 5/0042; A61B 5/02108; A61B 5/02416; A61B 5/0476; A61B 5/7225; A61B 5/7235; A61B 5/7257; A61B 5/0402; A61B 5/0816; A61B 5/165; A61B 5/746; A61B 5/0245; A61B 5/0452; A61B 5/0488; A61B 5/486; A61B 5/6824; A61B 5/6826; A61B 5/7285; A61B 5/742; A61B 8/06; A61B 5/026; A61B 5/0404; A61B 5/0432; A61B 5/0456; A61B 5/4035; A61B 5/681; A61B 5/0482; A61B 5/16; A61B 5/167; A61B 5/4094; A61B 5/0004; A61B 5/02405; A61B 5/02433; A61B 5/02438; A61B 5/7239; A61B 5/7264; A61B 5/7278; A61B 5/743; A61B 5/7475; A61B 5/113; A61B 5/08; A61B 5/087; A61B 5/0002; A61B 5/1118; A61B 5/4836; A61B 5/7267; A61B 5/7246; A61B 5/0024; A61B 5/4884; A61B 5/7221; A61B 5/74; A61B 5/7435; A61B 6/463; A61B 6/5205; A61B 6/5217; A61B 5/7405; A61B 5/11; A61B 2562/0219; A61B 7/003; A61B 5/726; A61B 5/7253; A61B 5/7415; A61B 5/02; A61B 5/721; A61B 5/0826; A61B 5/747; G06F 19/00; G06F 3/0488; G06F 15/18; G06F 19/3475; G06F 19/3418; G06F 3/015; G06F 3/04847; G06F 17/10; G06F 17/5009; G06F 19/30; G06F 19/3456; G06F 19/3481; G06F 1/163; G06F 3/041; G06F 3/0412; G06F 3/0416; G06F 3/0418; G06F 16/285; G06F 2203/011; G06F 7/02; G06F 7/60; G06F 7/68; G06F 17/18; G06F 18/00; G06F 18/26; G06F 18/28; G06F 18/285; G06F 18/20; G06F 2123/02; G05B 2219/23258; G05B 23/0221; G06N 5/047; G06N 99/005; G06N 3/02; G06N 3/006; G06N 3/0445; G06N 7/005; G06N 20/00; G06N 20/20; G06N 3/08; G06N 99/00;
   (Continued)

(56) References Cited

U.S. PATENT DOCUMENTS 6,554,763 B1 * 4/2003 Amano ................ A61M 21/00
                                                  600/26
6,607,484 B2 * 8/2003 Suzuki ................ A61B 5/6817
                                                  340/517

(Continued)

OTHER PUBLICATIONS

Kim, K. H. et al. Med Biol. Eng Comput. 2004 vol. 42 pp. 419-427.*

(Continued)

*Primary Examiner* — Mary K Zeman
(74) *Attorney, Agent, or Firm* — Thomas | Horstemeyer, LLP

(57) ABSTRACT

Various examples of methods and systems are provided for real-time signal processing. In one example, a method for processing data to select a pattern includes receiving data via a sensor, evaluating the data including waveforms over a time domain, averaging the waveforms to obtain a mean waveform, selecting a pattern based on the mean waveform, and generating a notification regarding the selected pattern. The pattern can include a start time, a hold time, and an end time. In another example, a system includes one or more sensors that detect the data and a mobile platform that evaluates the data, averages the waveforms to obtain the mean waveform and selects a pattern based on the mean waveform. A user interface can be used to communicate the notification regarding the selected pattern. The patterns can include breathing patterns, which can be used to reduce stress in a subject being monitored by the sensor.

23 Claims, 16 Drawing Sheets

(51) Int. Cl.
 A61B 5/259 (2021.01)
 A61B 3/16 (2006.01)
 A61B 8/00 (2006.01)
(52) U.S. Cl.
 CPC .......... *A61B 5/7203* (2013.01); *A61B 5/7235* (2013.01); *A61B 3/16* (2013.01); *A61B 8/00* (2013.01)
(58) Field of Classification Search
 CPC .... G06K 9/00335; G06K 9/0053; G06K 9/62; G06K 9/6262; H04L 67/12; H01L 41/1132; H04W 4/38; A61N 1/0492; A61N 1/36025; A61N 1/36071; A61N 1/36082; A61N 1/36125; A61N 1/36139; G16H 40/67; G16H 40/63; G16H 50/20; G16H 50/30; G16H 50/70; G16H 20/30; G16H 50/50; G16H 10/60; G16H 20/70; G08B 21/0453; G08B 21/0423; A63B 2230/04; A63B 2230/08; A63B 2230/40; A63B 2230/405; A63B 2230/42; A63B 2220/62; Y10S 128/92
 See application file for complete search history.

(56) References Cited

U.S. PATENT DOCUMENTS

| | | | | |
|---|---|---|---|---|
| 6,942,615 | B2* | 9/2005 | Suzuki | G06Q 30/0207 340/517 |
| 8,109,874 | B2* | 2/2012 | Kong | A61B 5/7435 128/920 |
| 8,340,746 | B2 | 12/2012 | Syed et al. | |
| 8,617,067 | B2* | 12/2013 | Jain | G16H 40/67 600/300 |
| 8,622,899 | B2* | 1/2014 | Jain | G16H 20/70 600/300 |
| 8,622,900 | B2* | 1/2014 | Jain | A61B 5/02055 600/300 |
| 11,197,633 | B2* | 12/2021 | Heneghan | A61B 5/0533 |
| 2001/0049471 | A1* | 12/2001 | Suzuki | A61B 5/11 600/300 |
| 2005/0033189 | A1* | 2/2005 | McCraty | A61B 5/16 600/509 |
| 2005/0113703 | A1* | 5/2005 | Farringdon | A61B 5/0428 600/509 |
| 2005/0124864 | A1* | 6/2005 | Mack | A61B 5/024 600/300 |
| 2013/0204146 | A1* | 8/2013 | Cho | A61B 5/7246 600/484 |
| 2017/0181654 | A1* | 6/2017 | Jun | A61B 5/04012 |
| 2017/0251987 | A1* | 9/2017 | Collier | A61B 5/165 |
| 2020/0335211 | A1* | 10/2020 | Gopalakrishnan | G16H 40/20 |
| 2021/0007667 | A1* | 1/2021 | Thaveeprungsriporn | A61B 5/4884 |
| 2021/0233641 | A1* | 7/2021 | Sasangohar | A61B 5/486 |

OTHER PUBLICATIONS

Naseri, H. et al. Med Biol Eng Comput (2013) vol. 51 pp. 1031-1042.*
Haag et al. in the book: Andre eds. Affective Dialogue Systems LNAI 2004, Springer. pp. 36-48.*
Allen, J.J.B, "Calculating metrics of cardiac chronotropy: A pragmatic overview", Psychophysiology, 39, S18, 2002.
Fink, W., "Stochastic Optimization Framework", Proc. SPIE, vol. 6960, 69600N, 2008.
Allen, J.J.B., et al., "The many metrics of cardiac chronotropy: A pragmatic primer and a brief comparison of metrics", Biological Psychology 74 (2007) 243-262.
Pan, J.P. et al., "A Real-Time QRS Detection Algorithm", IEEE Trans Biomed Engr, 22, pp. 230-236, 1985.
Brown, et al. "Breathing Practices for Treatment of Psychiatric and Stress-Related Medical Conditions" (Psychiatr Clin N Am 36 (Mar. 2013) 121-140).
Homma, et al. "Breathing rhythms and emotions" (Exp Physiol 93.9 (Aug. 2008) pp. 1011-1021).
Kjellgren, et al. "Wellness through a comprehensive Yogic breathing program—A controlled pilot trial" (BMC Complementary and Alternative Medicine (Dec. 2007) 7:43).
Van Diest, et al. "Inhalation/Exhalation Ratio Modulates the Effect of Slow Breathing on Heart Rate Variability and Relaxation" (Appl Psychophysiol Biofeedback (Aug. 2014) 39:171-180).

* cited by examiner

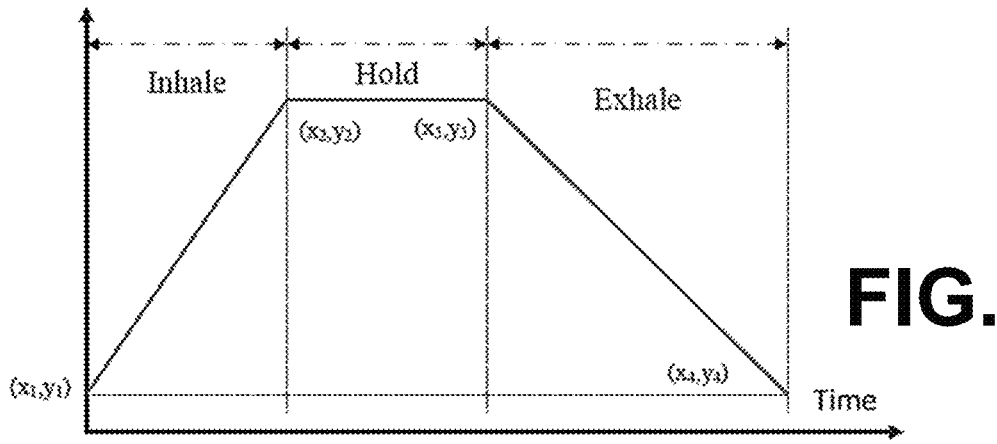

FIG. 12A

Algorithm 1: Finding best matching pattern

Input: one cycle actual respiratory waveform S;
Output: minL2NormAxis and minMaxErrAxis of four points for best matching pattern;

1: /* normalize S */
2: S <= S - min(S);
3: S_height = max(S);
4: S_length = length(S);
5: minL2Norm <= inf;
6: minMaxErr <= inf;
7: /* Loop to find pattern with min L2 norm and min Max error */
8: for i=0 to S_height do
9:   for j=0 to S_length-3 do
10:     for k=j+1 to S_length-2 do
11:       for p=k+1 to S_length-1 do
12:         for q=p+1 to S_length do
12:           /* generate a pattern waveform */
13:           tempPattern <= patternGenerate(i, j, k, p);
14:           /* compute L2 norm and min max error */
15:           tempMinL2Norm <= findL2Norm(S, tempPattern);
16:           tempMinMaxErr <= findMaxErr(S, tempPattern);
17:           if tempMinL2Norm < minL2Norm then
18:             minL2Norm <= tempMinL2Norm;
19:             minL2NormAxis <= [j, k, p, q];
20:           end if
21:           if tempMinMaxErr < minMaxErr then
22:             minMaxErr <= tempMinMaxErr;
23:             minMaxErrAxis <= [j, k, p, q];
24:           end if
25:         end for
26:       end for
27:     end for
28: end for
29: return minMaxErrAxis, minL2NormAxis;

FIG. 12B

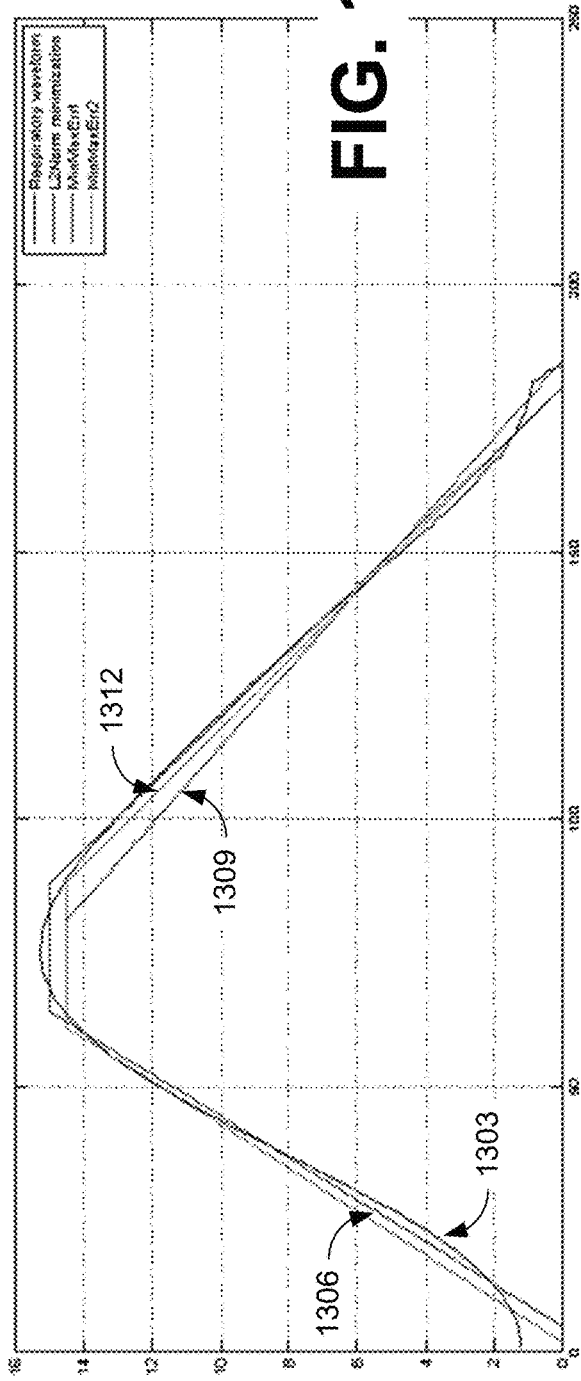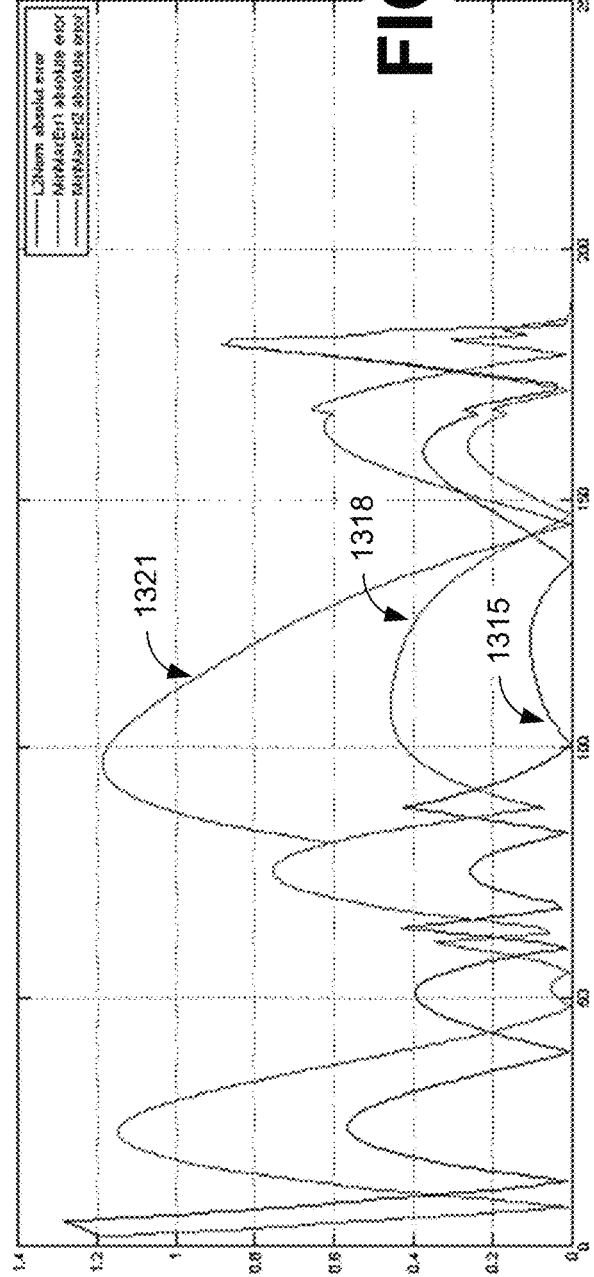

| TABLE I | Experimental results on raw signal and smoothed signal. | | | | | | | |
|---|---|---|---|---|---|---|---|---|
| | Raw signal | | | | IFFT Smoothed signal | | | |
| Secs | $X_1$ | $X_2$ | $X_3$ | $X_4$ | $X_1$ | $X_2$ | $X_3$ | $X_4$ |
| 150 | 2 | 63 | 87 | 181 | 5 | 64 | 87 | 180 |
| 112.5 | 2 | 65 | 102 | 184 | 4 | 68 | 101 | 176 |
| 100 | 3 | 62 | 95 | 171 | 2 | 62 | 89 | 182 |
| 75 | 8 | 61 | 90 | 176 | 2 | 62 | 91 | 182 |
| 50 | 2 | 72 | 99 | 188 | 2 | 71 | 100 | 188 |
| 37.5 | 2 | 58 | 98 | 177 | 2 | 58 | 98 | 177 |
| Std | 2.4 | 4.76 | 5.7 | 6.09 | 1.33 | 4.66 | 6.06 | 4.31 |

Std: standard deviation

SYSTEMS AND METHODS FOR REAL-TIME SIGNAL PROCESSING AND FITTING

CROSS REFERENCE TO RELATED APPLICATIONS

This application claims priority to, and the benefit of, U.S. provisional application entitled "REAL-TIME SIGNAL PROCESSING AND FITTING" having Ser. No. 62/171,895, filed Jun. 5, 2015, which is hereby incorporated by reference in its entirety.

BACKGROUND

Many people have experienced stress and have been affected negatively in their daily life and health. One key reason is because the human body is designed to respond to challenges and threats with an orchestrated set of physiological responses that facilitate adaptive behaviors. These responses are mediated by a system that includes a network of nerves connecting the brain and body. One part of the nervous system that slows the heart rate is called the vagus nerve. Activation of the vagus nerve can promote a relaxation response. It is possible to monitor vagus nerve activity using simple, inexpensive, and readily available technology such as wearable technologies, mobile platforms, and real-time data driven tracking and management systems. Monitoring and enabling vagus nerve activity has been found to be very useful in monitoring wound healing, post cardiovascular surgery recovery, and post-traumatic stress disorder.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 12A and 12B illustrate an example of pattern matching of an average respiratory waveform with breathing patterns of FIG. 5, in accordance with various embodiments of the present disclosure.

FIGS. 13A-13B, 14A-14B and 15A illustrate examples of optimal pattern matching, in accordance with various embodiments of the present disclosure.

DETAILED DESCRIPTION

Figure 1B:
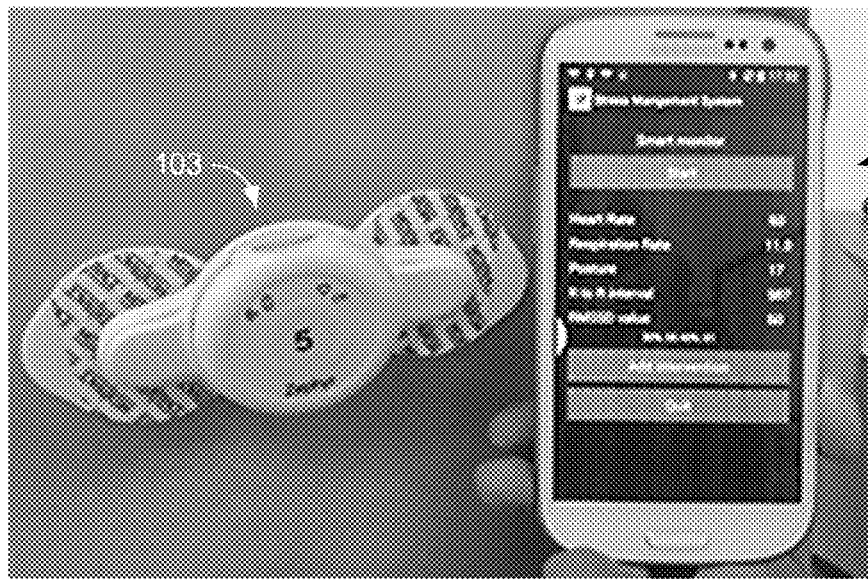
FIGS. 1A and 1B illustrate an example of a stress management system, in accordance with various embodiments of the present disclosure.

Disclosed herein are various embodiments related to signal processing, which may be applied to a variety of data, such as biometric data, medical sensor data, as well as radar, sonar, and lidar (light detection and ranging) data. Embodiments of the present disclosure allow for real-time (or near real-time) analysis of waveforms. Patterns or motifs can be identified in a stream of data and/or signals and used to initiate or control responses to the identified items. Applications range from medical signal processing, to identification of hidden items such as land mines or sea mines, to signal processing for space, aerial, land, water, and subsurface vehicles, objects or agents for, e.g., health, safety, navigational purposes, space situational awareness, astronomy, mining/resource exploration and exploitation, audio/acoustic identification, etc. One embodiment can relate to tuning or self-tuning of, e.g., devices, processes, and designs. Other embodiments relate to real-time waveform processing and fitting. Some embodiments relate to motif identification in signal processing. Yet other embodiments can relate to biofeedback-controlled interventions for medical or other purposes. For example, signal processing can be used for controlling a breathing apparatus during anesthesia via biofeedback control. The heart rate measurement can lead to an adjustment of the breathing apparatus operation frequency and volume, which in turn leads to an adjustment of the heart rate, etc. Reference will now be made in detail to the description of the embodiments as illustrated in the drawings, wherein like reference numbers indicate like parts throughout the several views.

Real-time data can be acquired through a wide range of systems and devices. In many cases, the data includes waveforms that are related to conditions or characteristics that can be used to control responsive or intervening activities. One example of this is in biomedical or healthcare monitoring of patients, where a variety of sensors can be used to monitor the subject. Wearable technology and mobile platforms can be used in various applications in clinical contexts such as disorder detection, treatment efficacy assessment, home rehabilitation and other health care research. Instead of distributed sensors, an integrated wearable unit including multiple sensors can be used. This can allow for simplification of the sensor design.

By wearing one integrated wearable sensor node or unit, for example heart rate, respiration rate, posture, activity and core temperature can be measured. For example, a Zephyr BioPatch integrates an ECG sensor, accelerometer and temperature sensor onto one chip. It is expected that the wearable technology works continuously for hours or days without interrupting the daily life of the monitored subject. In addition, the wearable sensor unit can be designed to provide high data acquisition rates. For example, 1000 Hz can be used for the ECG sensor sampling frequency with each sample represented as 10 bits for transmission and 12 bits binary for storage. In this disclosure, improved systems and methods are presented that use wearable technology and mobile platforms to monitor vagus nerve activity and increase its activity level when needed, or as desired, to promote relaxation and better health.

Various embodiments of the present disclosure allow for identification and selection of a response activity such as, e.g., exercises or other stress reduction methods for users based on real-time (or near real-time) analysis of waveforms. While the present disclosure may refer to respiratory data and breathing exercises, other types of sensor data and responsive activities are encompassed, such as tuning or self-tuning of, e.g., devices, processes, and designs. For example, an improved stress management system can collect user data including heart rate and respiratory rate, and transmit the data to a user device (e.g., a smartphone using Bluetooth) for further processing of the data. The stress management program can estimate the stress level of the subject based on heart rate variability and respiratory waveforms, and then provide relaxation exercises (e.g., YOGA breathing training or exercises) to help manage the stress.

Figure 1A:
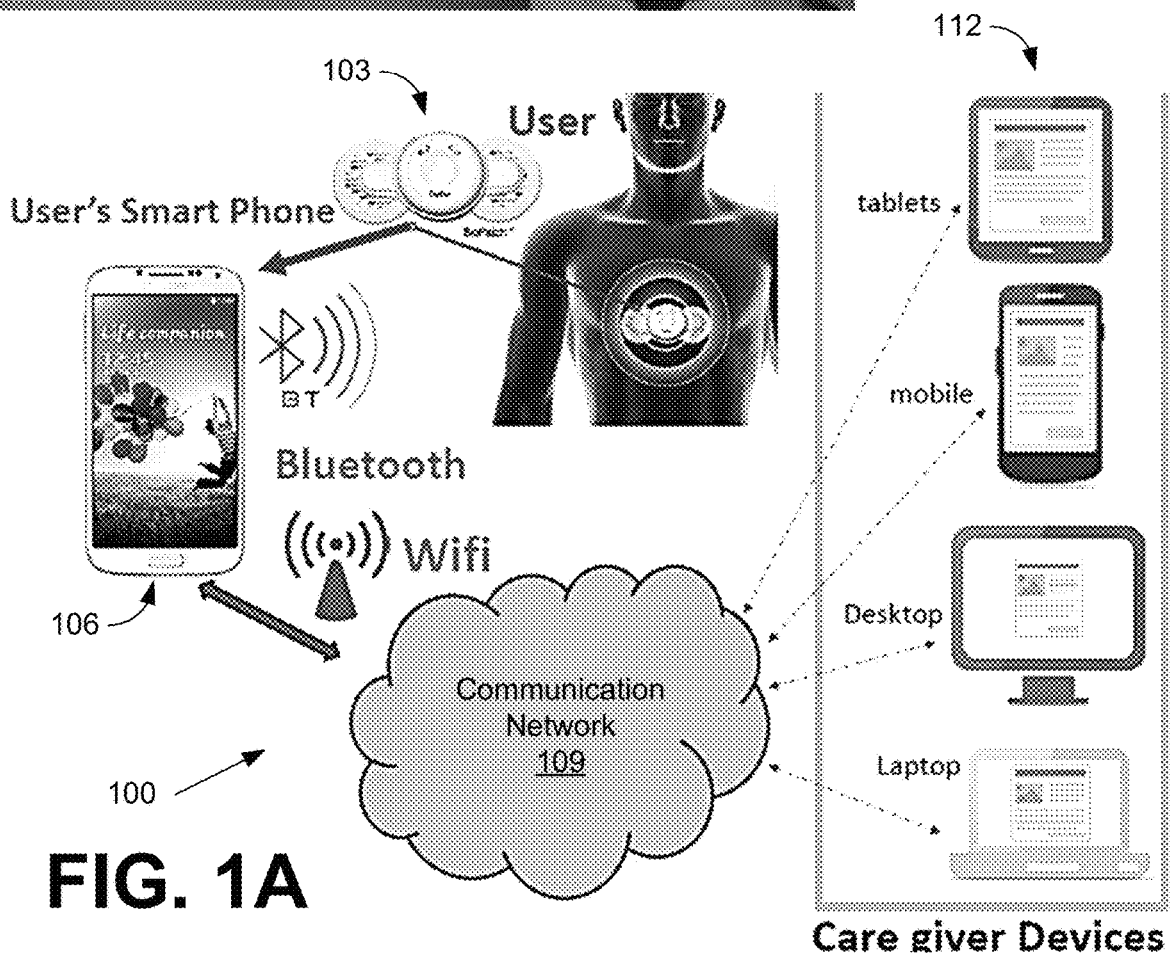

Referring to FIG. 1A, shown is an example of a stress management system 100. At the front end, wearable sensors 103 (e.g., a Zephyr BioPatch sensor) provide measurements of a patient's respiration rate, heart rate, body movements and other basic information. These wearable sensors 103 are low power and can work over 24 hours without charging to create baseline measurements for patients. In our current system, the smartphone or other mobile platform 106 accepts measurements from wearable sensors 103 through Bluetooth communications. Equipped with multiple cores and wireless data links, smartphones 106 provide communications to local data centers through a wireless data link (e.g., Bluetooth®, WiFi or cellular) to a network 109 (e.g., WLAN, cellular, intranet, internet, or other network) and enable basic data analysis capability locally on the smartphones 106. The cloud offers data storage for users and real time data monitoring and analysis for health care providers. For example, the smartphones can record the data, and transmit it through a wireless data link (e.g., Bluetooth®, WiFi or cellular) to a server backend for real-time (or near real-time) in depth analysis. The results of the analysis by the server backend can be sent back to the smartphone for display to the user. Text messages and warnings can be directly displayed on caregivers' smartphones or other devices 112 through software as a service (SaaS).

FIG. 1B is an image of the front end of the stress management system. Shown are a Zephyr BioPatch as the integrated wearable sensor node 103 and a Samsung smartphone as the mobile platform 106. The BioPatch has an integrated accelerometer, ECG circuit and temperature sensor on a single chip. With two standard ECG electrodes, the BioPatch can be attached onto the subject's chest and used to measure heart rate, respiration rate, posture, activity and core temperature of the subject. Wireless communication can be established between the BioPatch sensor 103 and the Samsung mobile phone 106 via a Bluetooth® link or other appropriate communication link. Note that the stress management system 100 can utilize other wearable sensors 103 and mobile platforms 106.

Figure 2A:
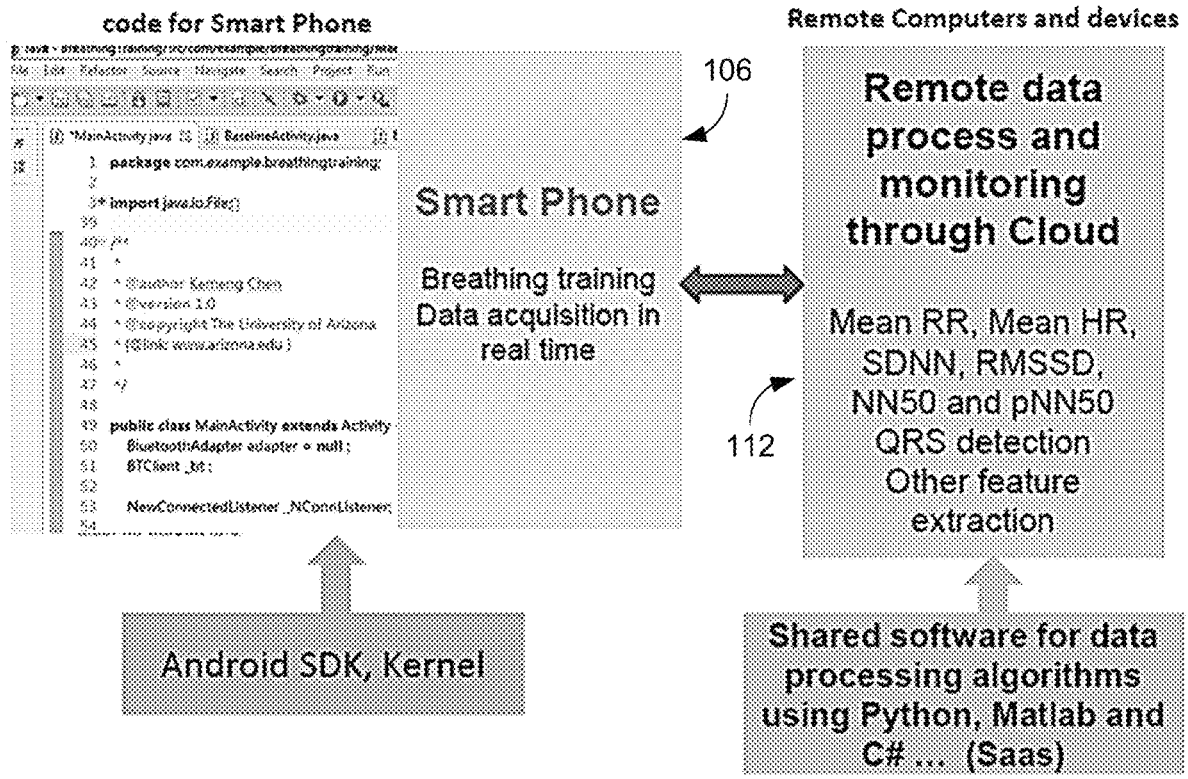
FIGS. 2A and 2B illustrate examples of programs or applications that can be utilized by the stress management system of FIGS. 1A and 1B, in accordance with various embodiments of the present disclosure.
Figure 2B:
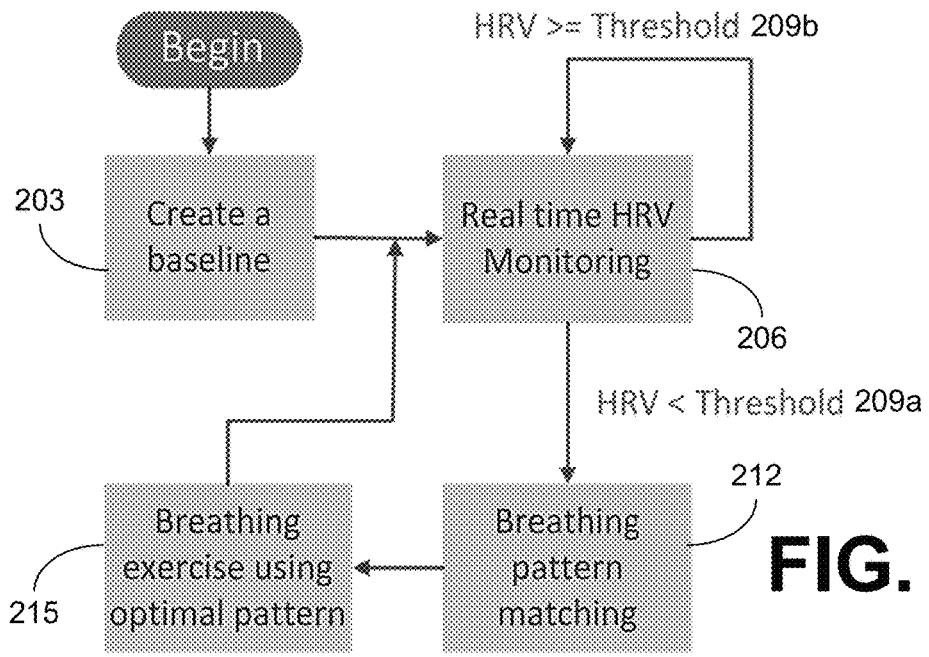
Figure 3:
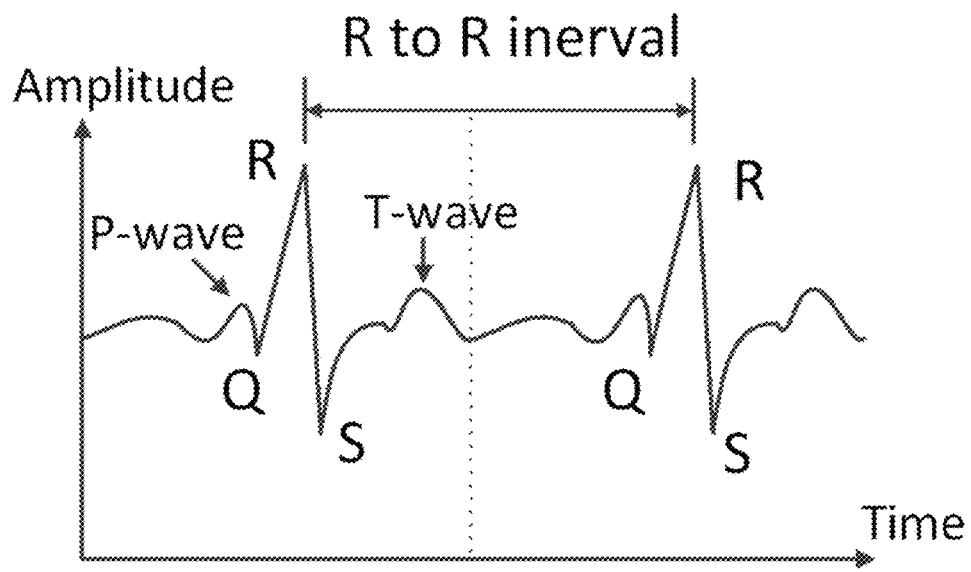
FIG. 3 is an example of electrocardiogram (ECG) waveforms, in accordance with various embodiments of the present disclosure.

FIGS. 2A and 2B illustrates various programs or applications that can be utilized by the stress management system 100. For example, an Android Operating system was used to create an Application Program Interface (API) between the wearable sensor node 103 and the smartphone 106, however other operating systems (e.g., Apple iOS) are equally applicable. Using remote processing, which can be provided via networked servers or other cloud processing technologies, various data analysis and mining approaches can be exploited to provide reliable stress level estimation. For example, a set of heart rate variability evaluations can be provided to detect and eliminate ECG noise. QRS (FIG. 3) detection algorithms can also be used to analyze Heart Rate Variability (HRV). HRV is an important parameter in many medical diagnoses and can be computed from successive heartbeats (also denoted as RR peak intervals). Accurate HRV estimation using raw Electrocardiogram (ECG) waveforms is still a difficult problem due to the noise in the raw ECG waveforms. ECG waveforms can be collected through electrodes attached to the body of a user. FIG. 3 shows two successive heartbeats of an ECG signal. As can be seen, each heartbeat includes a P-wave, a QRS complex, and a T-wave. QRS refers to the combination of the three graphic deflections on an ECG waveform. The time interval between the QRS complex peaks of two successive heartbeats is the RR interval.

Referring back to FIG. 2A, an index equipped database storage in local data center can facilitate remote data management and search. To perform real time monitoring and intervention, basic data analysis and feature filtering can be integrated in an application or "app" (e.g., code for the smartphone) that can be executed directly on the mobile platforms 106. For example, Root Mean Square of Successive Difference (RMSSD) can be used to assess HRV. The successive difference between inter-beat intervals is the definition of HRV. The successive difference between inter-beat intervals reflects how the timing of each beat is changing dynamically, attributable in large part to vagal influence. By taking the RMS of these successive differences, higher values reflect greater beat-to-beat variability, summarized by this computationally-efficient metric. As will be discussed, the RMSSD can be estimated/calculated at the mobile platform 103 (e.g., the Samsung phone) in FIG. 1B. Other more computationally intensive metrics can also be derived using remote computers/servers and services.

As illustrated in FIG. 2A, an application can be executed on a mobile platform 103 to perform front end real time stress management. FIG. 2B shows a flow chart illustrating an example of the architecture, functionality, and operation of a possible implementation of the mobile platform app. Initially, a baseline assessment 203 can be performed based upon measurements of the test subject. Real-time (or near real-time) HRV monitoring is carried out at 206. First, a data stream is received from the wearable sensor node 103. Then, the RMSSD computation can be performed on the mobile platform 106.

A RMSSD threshold 209 is setup for each user based on one's baseline assessment 203. This threshold 209 is used to identify whether one is stressed or not. If the user is identified as "stressed" 209a, a breathing pattern matching algorithm 212, for example, can be activated to identify the optimal breathing exercise 215 for the user based on his/her respiratory waveform. If the user's stress level drops to normal 209*b*, the exercise will stop. Real-time HRV monitoring 206 continues throughout, i.e., before, during, and after the exercise. This whole monitoring and exercising process can be referred to as "stress intervention". While there are many breathing exercises that may be used, without the loss of generality this disclosure focuses on YOGA breathing exercises as an example for stress intervention. Studies have shown that low HRV is an indication of high stress level, and a breathing exercise can help the user increase HRV and relieve stress.

Integrated Wearable Sensor Node. Wearable sensors 103 stream real-time data to mobile platforms 106 via low-power and reliable wireless interfaces. Without interrupting the users' daily life, these sensors 103 are expected to work continuously for hours or days. In addition to the long working hours, we also design wearable sensors to have high data acquisition rates. For example, in the implemented stress management system, a frequency of 1000 Hz for ECG sensor sampling was used with each sample represented as 10 bits for transmission and 12 bits binary for storage. Instead of using distributed body sensors, integrated wearable sensors 103 (e.g., BioPatch) were chosen with an ECG sensor, accelerometer, and temperature sensor integrated onto one chip. Instead of designing a separate sensor for respiration rate, impedance pneumography can be implemented by using the signal passing through the same electrodes of the ECG sensor. Hence, by wearing one integrated wearable sensor node 103, it is possible to measure heart rate, respiration rate, posture, activity, and core temperature at the same time. This allows time correlations between these and other parameters to be observed and analyzed. It should be pointed out though that, in other embodiments, a plurality of individual sensors with at least one measured parameter each could be employed as well. Each sensor can be connected to the mobile platform 106 via low-power and reliable wireless interfaces.

Battery life and weight are also important features for wearable sensors 103. Most integrated wearable sensor nodes 103 use an internal lithium cell battery. Different data transmitting modes can affect battery life by over 30%. For example, data packets can record sensory data into flits as in a BioPatch. Each flit contains a header that specifies the type and the size of the data. Signals such as ECG, respiratory waveform, posture, temperature, etc. are stored as packets. The integrated wearable sensor node 103 can transmit one packet to a mobile platform 106 per second. The size of the data packet will be determined by each sensor's sampling rate. By using low sampling rates for slowly changing signals, such as body temperature, the data packet size can be reduced which in turn reduces packet transmission time and power consumption during data transmission.

QRS detection and Heart Rate Variability for off-line calibration. Because HRV is employed to assess stress level, it may be important to calibrate the HRV estimation. HRV can be evaluated by using R to R peak intervals in the ECG signal. FIG. 3 illustrates two QRS complexes and the R to R peak interval between the two R peaks.

The RMSSD value is used to evaluate the changes between the two R peaks (the inter-beat intervals) over time. Computation of RMSSD follows the root mean square of successive differences as given by:

$$RMSSD = \sqrt{\frac{1}{N-1}\left(\sum_{i=1}^{N-1}((R_{i+1} - R_i) - (R_i - R_{i-1}))^2\right)} \quad (1)$$

where N is the number of R to R peak samples within a defined time window.

In the stress management system 100, raw ECG signals are acquired from the integrated wearable sensor node 103 and used for QRS detection. Automatic QRS complex detection is a difficult task due to muscle movement, power line inference, and electrode artifacts from motion and high P or T-wave. Accurate QRS detection algorithms can be used to assure reliable HRV estimation. This step can also be performed off-line to calibrate the HRV estimation for the real-time stress management system. For example, QRSTool (see, e.g., "Calculating metrics of cardiac chronotropy: A pragmatic overview" by J. J. B. Allen (Psychophysiology, 39, S18, 2002), which is hereby incorporated by reference in its entirety) can be used as the off-line calibration tool for the HRV estimation. The QRSTool employs a peri-beat average QRS complex detection algorithm, which generates an average beat template and applies this template to the rest of ECG to identify other QRS complexes. In order to obtain a good average beat template, the QRSTool allows manual modification of beat detection to insert missing beats or delete redundant beats. The QRSTool first uses a hard threshold for a number of successive beats (e.g., a 30 second long ECG) to detect the QRS complex given that change from baseline would not affect ECG within a short period of time. Based on these detected QRS complexes (beats), the algorithm can extract each individual heart beat based on pre- and post-beat length (80 ms to 250 ms) and then estimates an average prototype beat vector. Next, the algorithm filters the entire ECG waveform and generates another feature series. Finally, the R spikes can be extracted from the feature series. The QRSTool can also allow for correction of artifacts (e.g., the introduction of high magnitude noise from tapping or brushing the subject's chest) to improve the robustness of the detection algorithm. Other calibration and/or error/artifact correction methods and algorithms known to the ones skilled in the art may be employed.

While the RMSSD value is used to assess the stress level to activate YOGA breathing exercise, this paced intentional breathing also introduces changes in the various performance metrics used to assess vagal control. In the stress management system 100, a baseline HRV measurement 203 (FIG. 2B) can be created when the user is under spontaneous conditions. Thus, the subject's breathing becomes a key indicator that allows the stress management system 100 to discover the vagal system impact on variability in cardiac rate.

Figure 4:
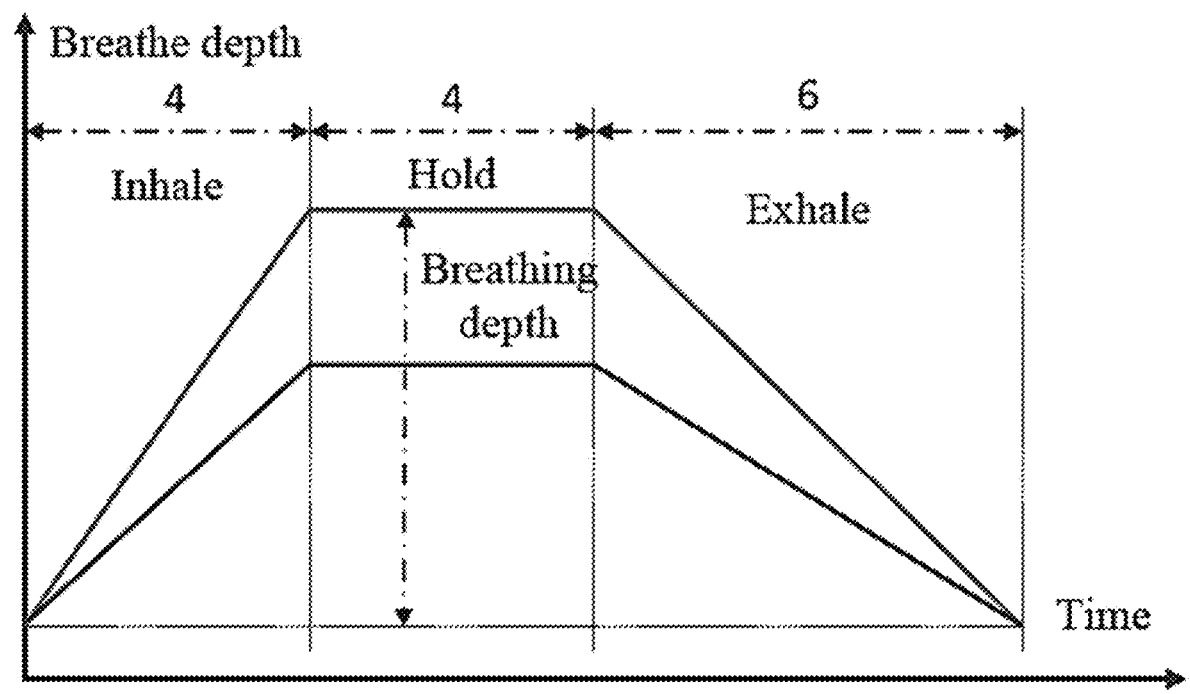
FIGS. 4 and 5 are examples of breathing patterns that can be used for stress relief, in accordance with various embodiments of the present disclosure.

The stress management system 100 estimates stress level based on heart rate variability and respiratory waveforms, and then provides relaxation exercises such as YOGA breathing trainings to help manage stress. Breathing exercise has been shown to be an effective way to relieve stress and help people calm down. During the breathing exercise, the subject is required to breathe strictly following one selected exercise. One popular type of breathing exercise that may be used is referred to as YOGA exercise. FIG. 4 shows an example of a breathing pattern that can be used as a YOGA exercise. Breathing patterns include three parts: inhale, hold, and exhale, which can be represented as a trapezoidal waveform. The horizontal axis represents the time and the vertical axis is the breathing depth. One breathing cycle is defined as a repeated, complete breathing pattern. This concept of a breathing pattern can be used to illustrate the differences between different YOGA exercises.

Figure 5:
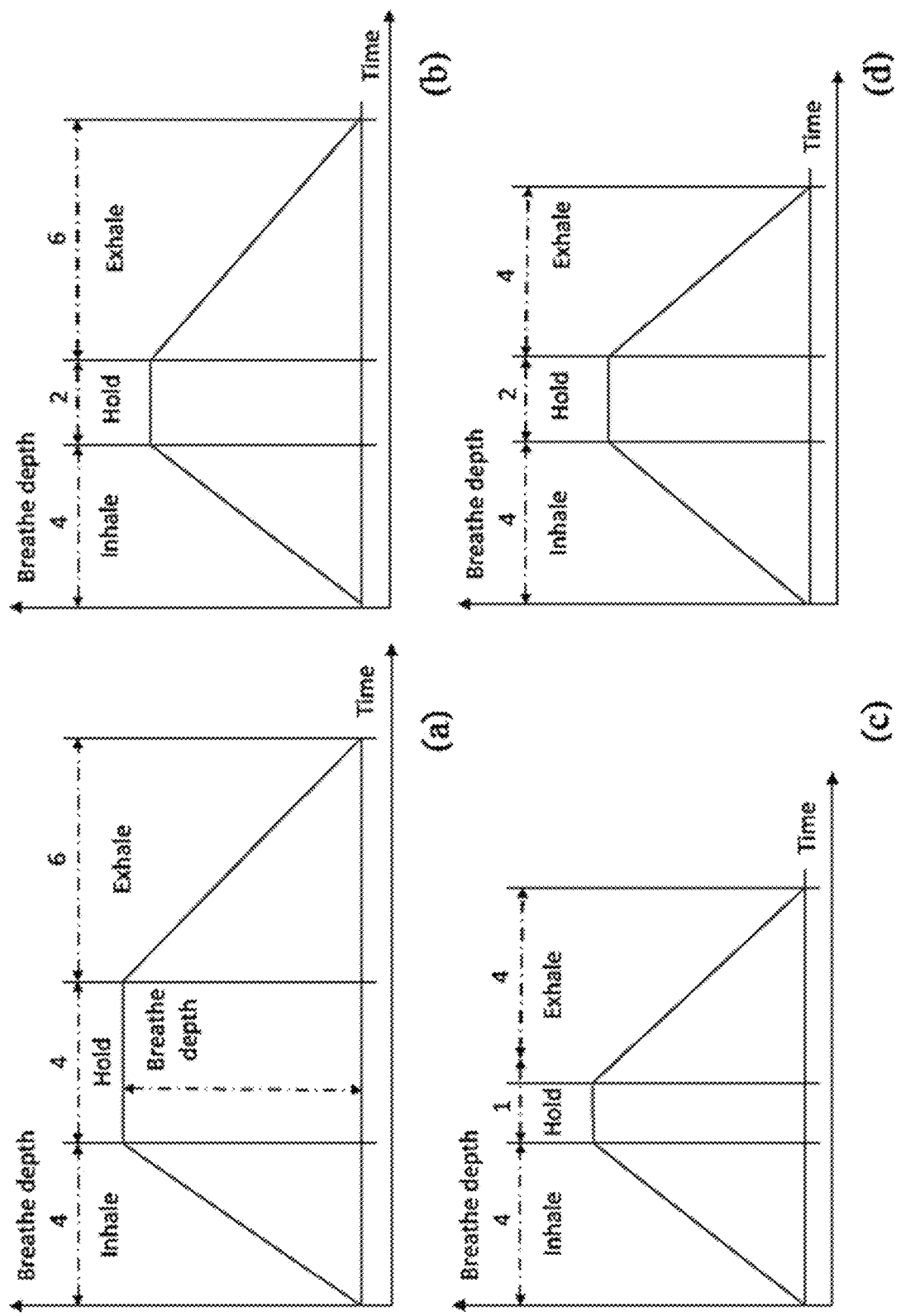

FIG. 5 illustrates several exemplary, different YOGA breathing exercises that may be available for users. Specifically, each breathing pattern is illustrated as real-time respiratory waveforms, which can be used to identify which breathing patterns may be best-suited for a particular user. Such signal patterns can be used as a basis for tuning or self-tuning of, e.g., devices, processes, and designs in general. FIGS. 4 and 5(a) show a 4-4-6 pattern with an inhale time, a hold time, and an exhale time of 4 seconds, 4 seconds and 6 seconds, respectively. The other three YOGA exercises in FIGS. 5(b), 5(c) and 5(d) show the 4-2-6 pattern, 4-1-4 pattern, and 4-2-4 pattern, respectively.

While all YOGA exercises can be represented by the trapezoidal waveforms, it should be noted that a wide range of YOGA exercises are possible with diverse lengths of time and breathing depths. It is also important to note that each test subject (user or patient) doing the same YOGA exercise may lead to a different breathing depth and slopes of the respiratory waveforms. For instance, if two test subjects closely follow the same YOGA exercise, the only things in common in their respiratory waveforms may be the inhale time, the hold time, and exhale time. FIG. 4 illustrates the respiratory waveforms from two users that followed the same YOGA exercise 4-4-6 pattern, but which led to two different respiratory waveforms (different depths) even though the same inhale hold and exhale times were observed. By understanding these differences, the best breathing exercise can be identified for the test subject such that the inhale time, hold time and exhale time are very similar to the test subject's original respiratory waveform.

Figure 6:
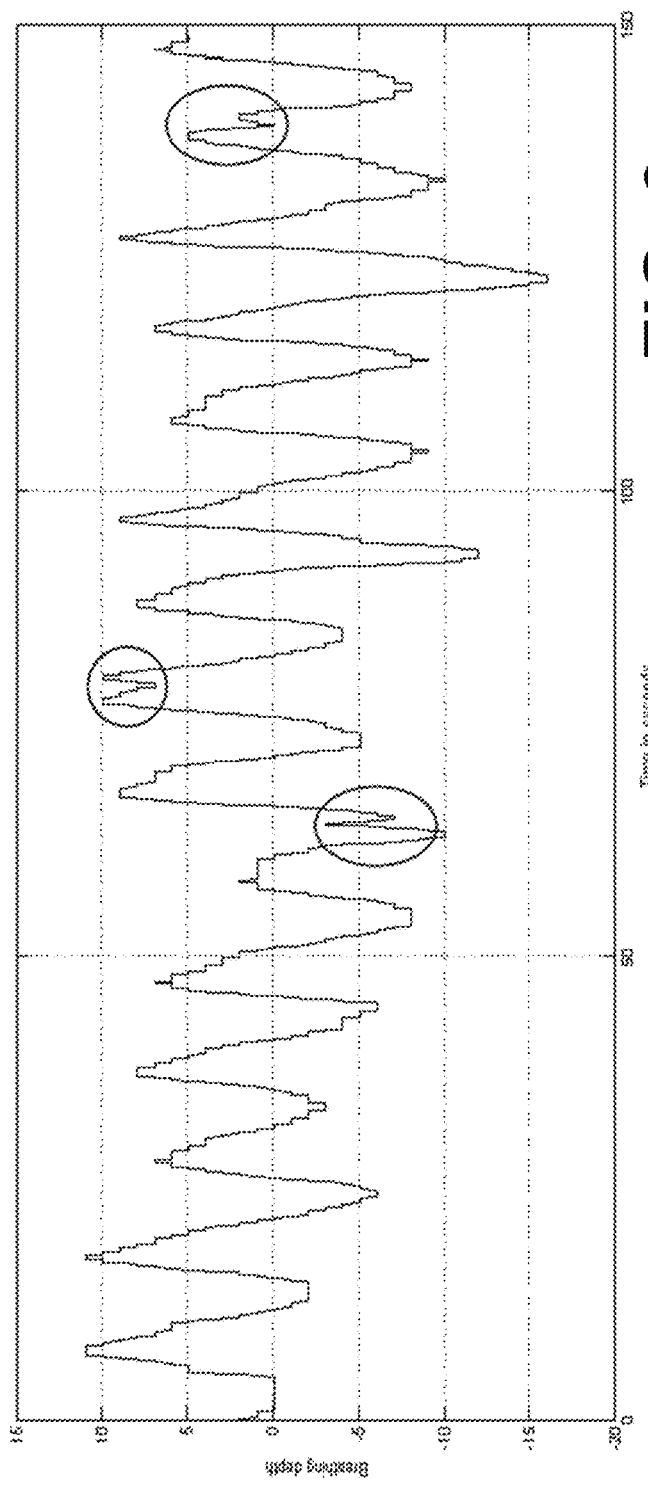
FIGS. 6 through 9 illustrate examples of noise removal from data obtained by a sensor of FIGS. 1A and 1B, in accordance with various embodiments of the present disclosure.

Identify cycles for respiratory waveforms. Different individuals may have different breathing cycles, which may be discovered from raw respiratory waveforms. In that regard, wearable sensors 103 can detect and represent a subject's breathing activities as respiratory waveforms in the time domain. Various uncertainties during measurement and high sensitivity of the wearable sensors 103 may cause much of the noise occurring in the respiratory waveforms. FIG. 6 shows an example of a noisy, raw respiratory waveform with fourteen cycles in the time domain. The horizontal axis represents the time in seconds and the vertical axis represents breathing depth. From observation, each peak represents one breathing cycle with the noise highlighted in the circled locations. However, due to the various noise signals with different amplitude and frequencies in the raw data, it is not trivial to identify cycles by directly searching for peaks and valleys in the time domain.

As can be seen from FIG. 6, such noise signals have higher frequencies than the regular cycles. For example, all three circled areas have split peaks that occur more frequently in the time domain than the regular cycles. Therefore, in one instantiation, the time domain waveform can be transformed to the frequency domain using a Fourier transform after subtracting the mean value of the raw respiratory waveform. The mean value of the raw respiratory waveform can represent the DC offset of the data, which may also be regarded as the zero frequency component (also known as the DC (or direct current) component). The DC component of the raw respiratory waveform can be several orders of magnitude higher than other frequency coefficients. In general, the design of a sensor 103 determines the DC component.

Figure 7:
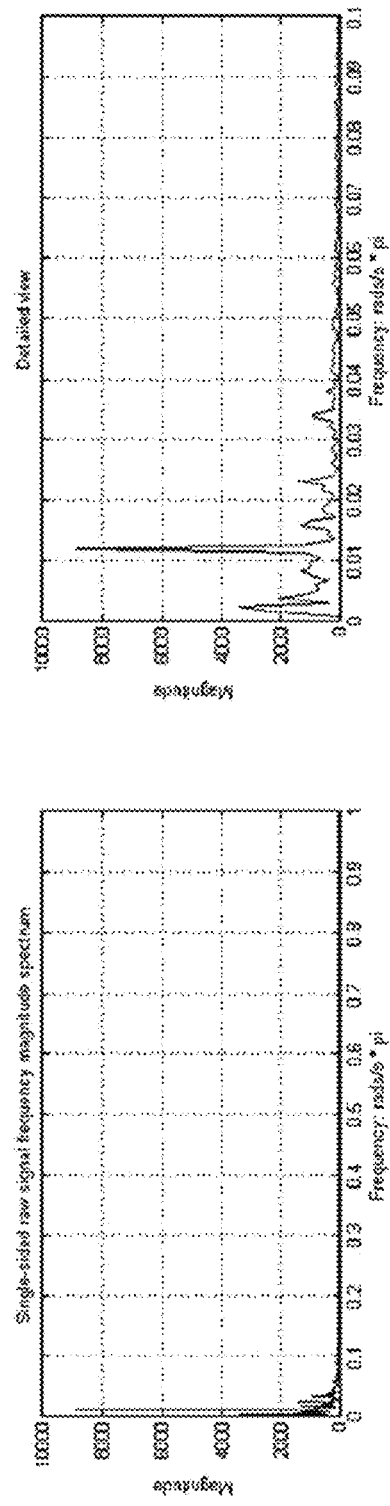

In this case, as impedance pneumography may be used as an example to detect respiration rate and to generate respiratory waveforms, the DC response of the user's chest area and electrodes decides the DC component. In order to ensure the accuracy of other frequency coefficients, the DC component may be removed by subtracting the mean value of the raw respiratory waveform. Subsequently, the processing of the respiratory waveform data may proceed. FIG. 7 illustrates an example of the single-sided frequency spectrum of the raw respiratory waveform. FIG. 7(a) shows the single-sided frequency spectrum from 0 to $\pi$ and FIG. 7(b) demonstrates a zoom-in view of the frequency coefficients from 0 to $\pi/10$.

Due to the symmetric property of the Discrete Fourier Transform (DFT), the coefficients from 0 to $\pi$ are the same as the ones from $\pi$ to $2\pi$. As shown in FIG. 7(a), the magnitude of the frequency coefficients drops very fast from the large coefficients to the small ones. This indicates that a small portion of the coefficients are more significant than the rest. Therefore, the noise in the frequency domain can be removed by keeping only the most significant coefficients. Without the loss of generality, it may be assumed that any raw respiratory waveform is a combination of the clean waveform and noise. In most cases, it may be assumed that the noise signals are additive ones, and are less significant than the clean waveform without noise. Therefore, the noise may be removed in the frequency domain by keeping only the most significant coefficients.

Figure 8:
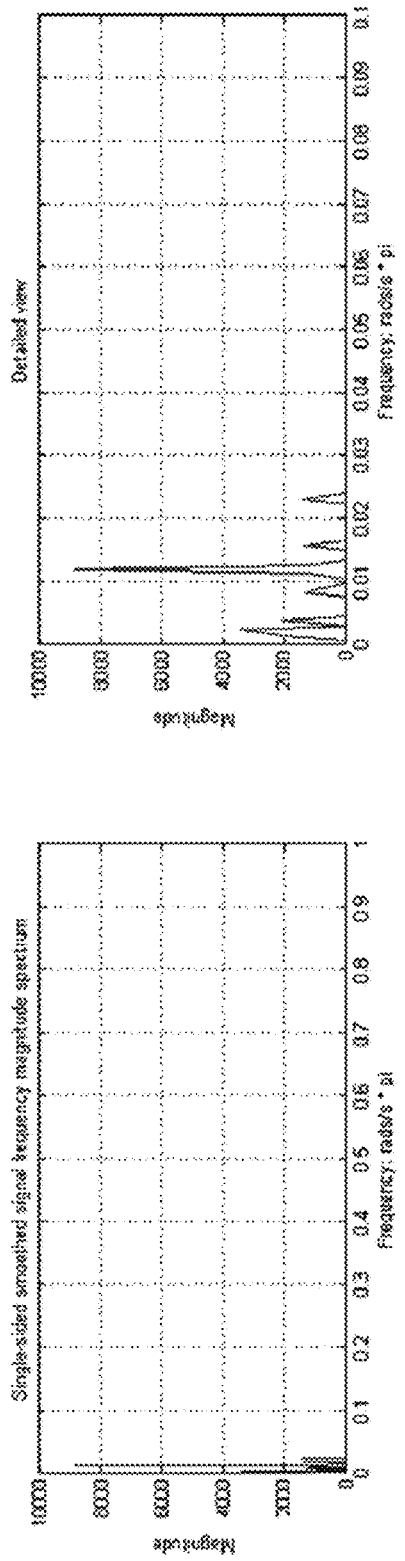
Figure 9:
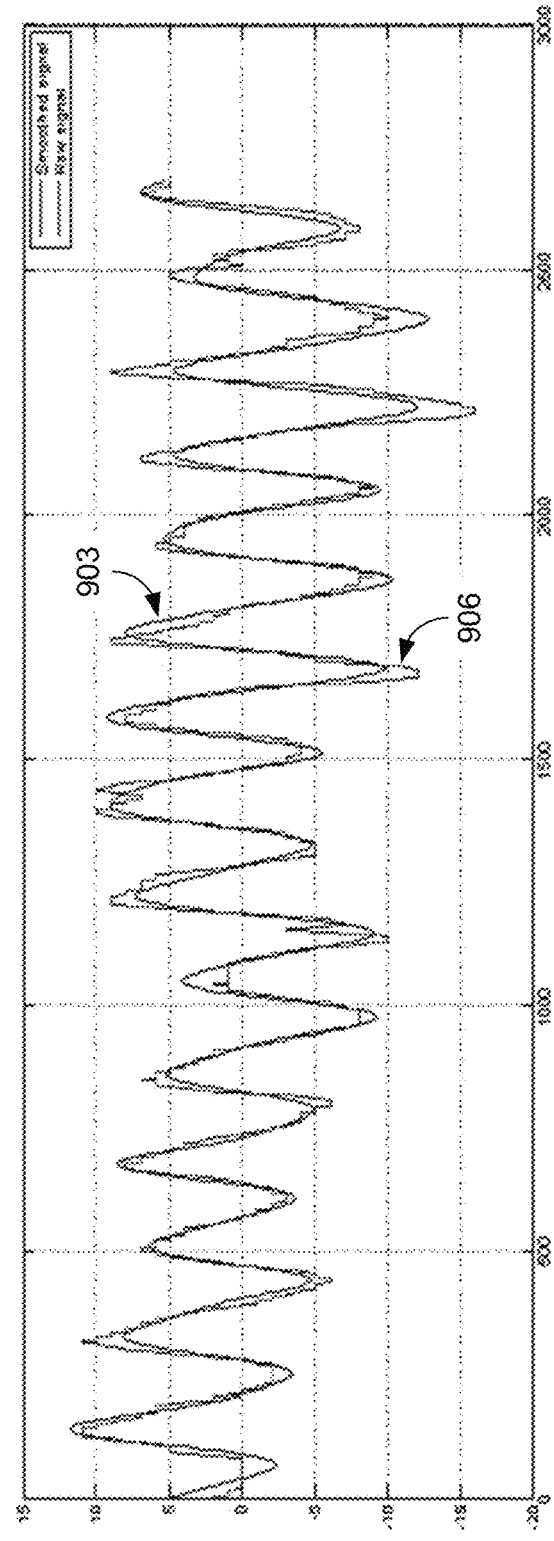

FIG. 8 shows an example of the single-sided frequency spectrum after removing less significant coefficients. In this case, as an example, only the leading ten most significant coefficients have been kept. In other implementations, more or less signification coefficients may be retained. FIG. 8(a) shows the single-sided frequency spectrum from 0 to $\pi$ with FIG. 8(b) demonstrating the reduced set of frequency coefficients from 0 to $\pi/10$. FIG. 9 displays the result of the Inverse Fourier Transform (IFT) using the ten most significant coefficients of FIG. 8. As illustrated, the resulting waveform 903 is very smooth. The processed waveform 903 can be compared with the original raw respiratory waveform 906. The processed waveform 903 matches with the original waveform 906 with little noise. The breathing cycle can now be identified using the processed waveform 903.

Figure 10:
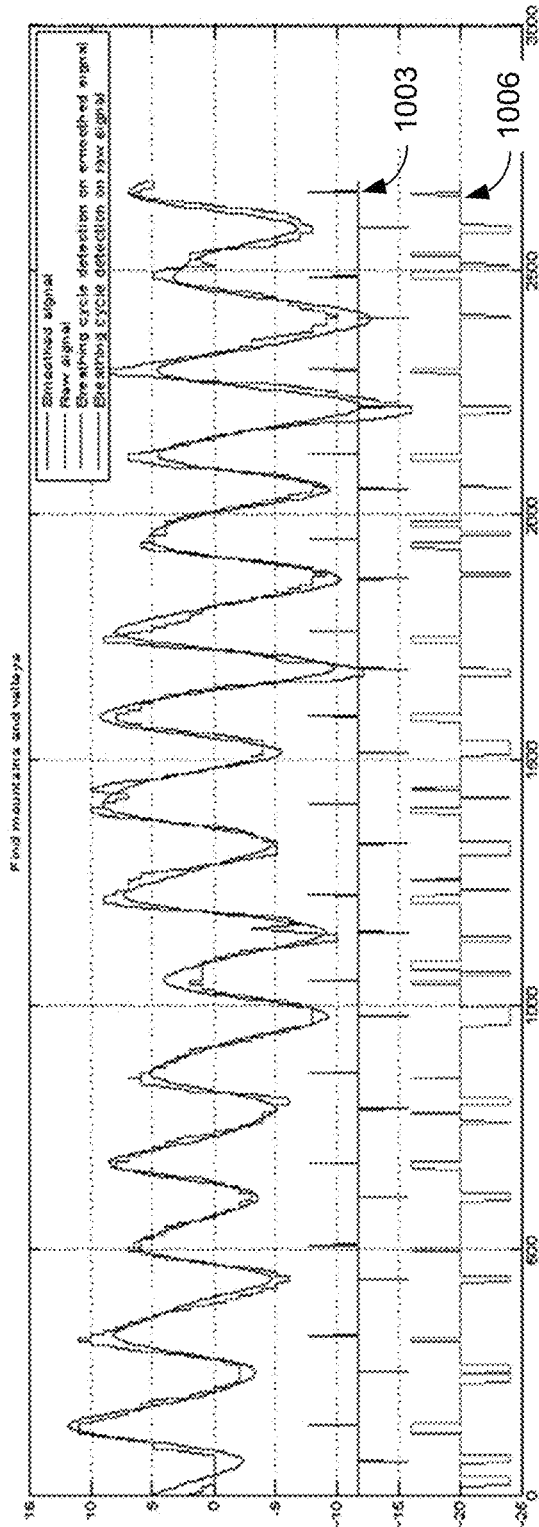
FIG. 10 illustrates an example of the evaluation of waveforms of the data in FIG. 9 based upon Inverse Fourier Transform (IFT) with subsequent valley and peak detection, in accordance with various embodiments of the present disclosure.

By locating the valleys in the smoothed waveform, the starting point and the end point of each cycle can be found. As such, the valley detection method allows for removal of noise and defects from the new processed waveform. To illustrate in a formal way, assume that $S=\{s_1, s_2, \ldots, s_n\}$ represents a group of sample points in the time domain of the processed waveform. Then, any $s_i (i \in (2, n-1))$ that satisfies $(s_i < s_{i-1}$ AND $s_i < s_{i+1})$ is identified as a valley. A similar idea can be applied to identify peaks in the processed waveform. FIG. 10 illustrates an example of the results of the identified breathing cycles (plot 1003). Vertical lines of 1003 represent the valleys' and peaks' respective occurring times.

One breathing cycle can be identified by two downward pointing vertical lines. The same detection algorithm can be applied to the original raw respiratory waveform: Here, due to noise, the resulting indications of valleys and peaks are mixed with noise-caused valleys and noise-caused peaks, resulting in spread out peaks (plot 1006). The smoothed waveform may therefore be used to mark the starting and ending point of each cycle, and those marks may be used to extract breathing cycles from both the raw respiratory waveform and the IFT-smoothed waveform.

Figure 11:
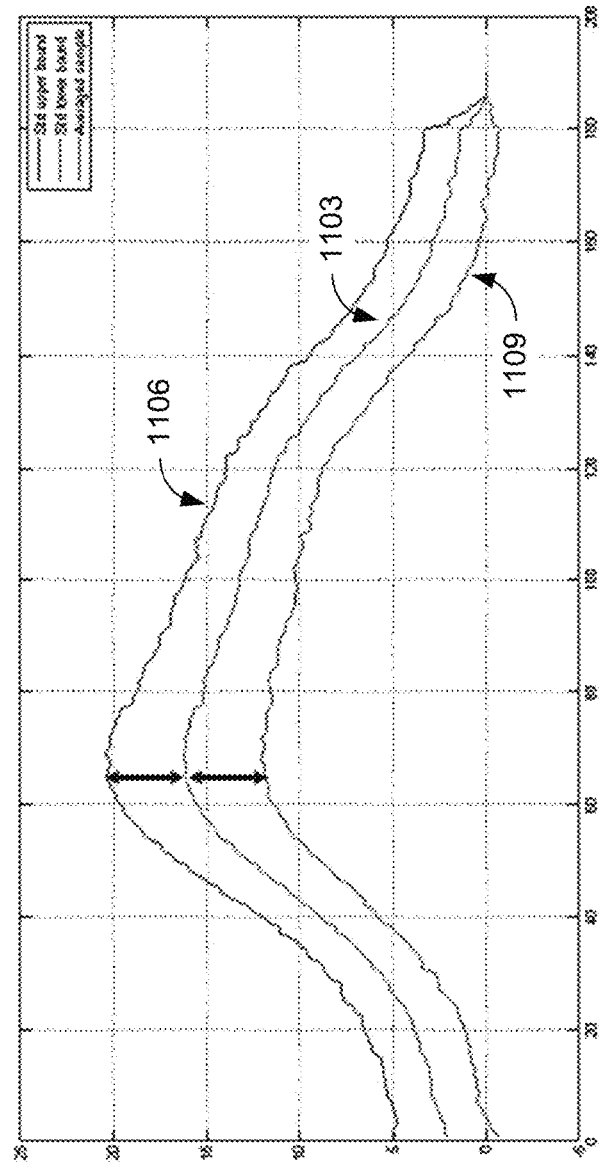
FIG. 11 is an example of an average respiratory waveform, in accordance with various embodiments of the present disclosure.

Identify inhale time, hold time, and exhale time for the original raw respiratory waveform. Given several different cycles of raw respiratory waveforms, a breathing pattern (inhale time, hold time, and exhale time) can be identified for a user. Due to the variations in each cycle of the raw waveform, the average of a set of respiratory waveforms cycles can be computed to get the mean respiratory waveform. As a first step, a left-side alignment can be performed for a group of breathing cycles of the raw respiratory waveform to ensure that the pattern starts with the beginning of an inhale cycle. FIG. 11 shows an example of the average respiratory waveform (curve 1103) with upper bound (curve 1106) and lower bound (curve 1109) derived from standard deviations. The variations mainly affect the breathing depth but have little influence on the inhale time, the hold time, and the exhale time. Thus, it can be concluded that by using an average respiratory waveform, accurate inhale, hold, and exhale times can be identified.

Because the breathing exercises can be represented as one out of, e.g., four (or more) different trapezoidal waveforms (e.g., YOGA breathing pattern), one of the trapezoidal waveforms (e.g., YOGA breathing pattern) can be found that fits the average respiratory waveform in an "optimal" way (i.e., with minimum error). There are at least two ways to achieve minimum error: minimizing L2-norm to get the least error, or minimizing the maximum single occurring error. Equation (2) represents the L2-norm method, while the min-max error approach is given in equation (3).

$$\min \sum_{i=1}^{N-1} (S_i - D_i)^2 \qquad (2)$$

$$\min\left(\max_{i \in \{1 \ldots N\}} (|S_i - D_i|)\right) \qquad (3)$$

where each $S_i$ is a data point in the average respiratory waveform and $D_i$ is a data point in one of the trapezoidal waveforms (i.e., YOGA pattern). The end results of the above two equations are the optimal trapezoidal waveforms that can have the least respective error (from among the group of trapezoidal waveforms). The proposed algorithm uses four representative points to represent a trapezoidal waveform: $(x_1, y_1)$, $(x_2, y_2)$, $(x_3, y_3)$, and $(x_4, y_4)$ as shown in FIG. 12A. The first and second points determine the inhale time; the second and third points determine the hold time; and the third and fourth points determine the exhale time. Note that the first and fourth points should have the same height which means $y_1=y_4$ and the second and third points should also have the same height as shown in FIG. 12A.

Referring next to FIG. 12B, shown is pseudo code of an example of the proposed algorithms. When performance of the two error minimization algorithms was compared, it was found that the L2-norm based error minimization approach outperformed the min-max error algorithm. First, degeneracy situations may occur in the min-max error approach of equation (3) when two trapezoidal waveforms share the same maximum error value at different locations of the original raw waveforms. Instead of focusing on the maximum error, the L2-norm minimization method sums up all the errors occurring at different locations of the waveforms. It is therefore unlikely or less likely that two different trapezoidal waveforms will have the same minimum error in L2-norm.

In addition to the degeneracy issue, the potential alignment-caused errors (e.g., left-side alignment) may also affect the outcome of the error minimization procedure. To illustrate, the test subject may not finish the exhale action completely before his/her next breathing cycle. This may lead to errors at the starting point and the end point. These types of errors may not cause major issues when L2-norm based error minimization is used as it sums up all errors in the form of $(S_i-D_i)^2$ as shown in equation (2). The errors occurring at the beginning and the end point of each cycle only contribute to two error values in this summation. However, if such type of errors happen to be the maximum of $|S_i-D_i|$, then the outcome of the min-max error of equation (3) may be affected more significantly.

FIG. 13A shows an example of a degeneracy case that happened when using the min-max error method. Curve 1303 is the original raw respiratory waveform, and curve 1306 is the optimal result generated by the L2-norm error minimization method. Curves 1309 and 1312 are two different trapezoidal waveforms generated by the min-max error method of equation (3) that have the same maximum single occurring error but at different time points and thus are two degenerate cases. This is a degeneracy case that was caused by errors at the beginning of the respiratory waveform. In order to find the maximal error, FIG. 13B shows the absolute errors between the respiratory waveform and best fit trapezoidal. Here, curve 1315 is the absolute error between the original respiratory waveform and the L2-norm identified best trapezoidal waveform. The curves 1318 and 1321 are the absolute error between the original respiratory waveform and the two results from the min-max approach.

Figure 14A:
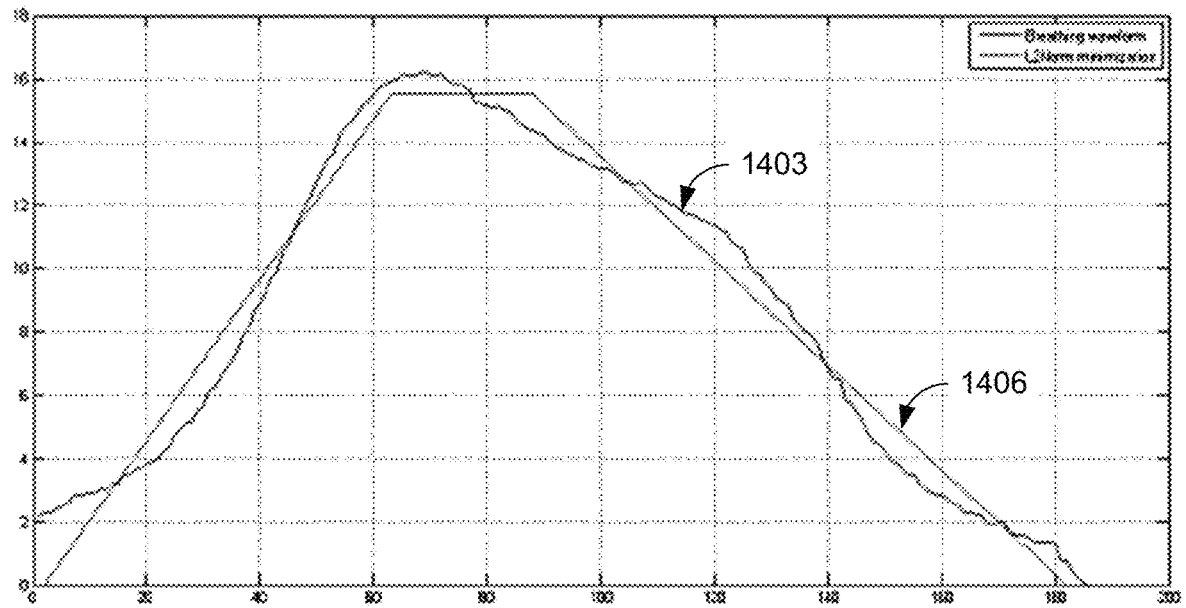
Figure 14B:
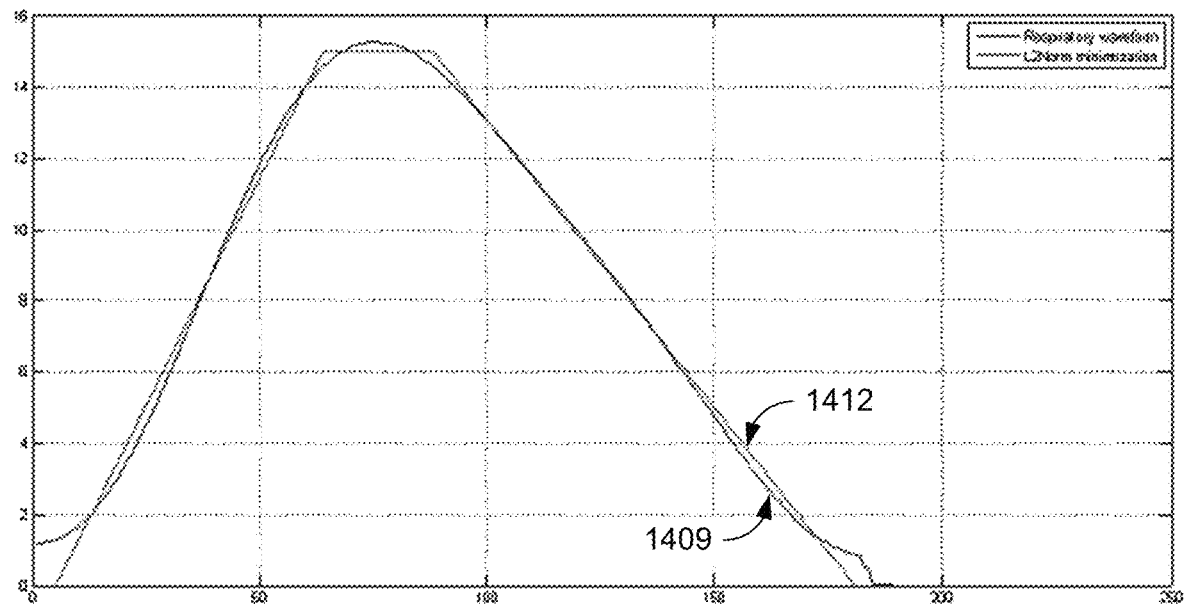

Identify the best matching breathing exercise pattern. Given raw respiratory waveform data from a subject, the best breathing exercise for the subject can be found. FIG. 14A shows an example of the L2-norm minimization result with the optimal trapezoidal waveform compared with the average respiratory waveform. Plot 1403 is the average waveform of the raw respiratory waveform data, and plot 1406 is the best trapezoidal waveform with minimum error. The x-axis values for the four representative points are 2, 63, 87, and 181, respectively. FIG. 14B shows the L2-norm minimization result with the optimal trapezoidal waveform compared with the smoothed average respiratory waveform 1409. Plot 1412 is the best trapezoidal waveform with minimum error. The x-axis values (i.e., time) for the four representative points are 5, 64, 87, and 180, respectively.

Since the wearable sensor 103 (FIGS. 1A and 1B) works at a fixed sampling rate ($f_s$), the inhale time, the hold time, and the exhale time can be computed using the four points. For example, the inhale time can be computed as $(x_2-x_1)/f_s$. The hold time can be estimated as $(x_3-x_2)/f_s$, and the exhale time can be determined as $(x_4-x_3)/f_s$. The time duration of the three breathing times can be mapped into a three-dimensional vector space to then find the minimum Euclidean distance between the best trapezoidal waveform and the four breathing exercises, i.e., YOGA patterns.

For validation, the stress management system 100 was implemented on an Android OS 4.3 executing on a Samsung Galaxy III version using JAVA and Android SDK as the mobile platform 106. A Zephyr BioPatch 3.0 was selected as the integrated wearable sensor nodes 103. The sensor 103 collected ECG data at 1000 Hz, respiratory waveforms at 18 Hz, together with other signals. It was equipped with Bluetooth working at 2.4 to 2.83 GHz. Data packets used the standard RIFF format and packet transmission rate was 1 second. The battery life was approximately 22 hours with Bluetooth wireless communication. The algorithm to find best fitting breathing exercise was implemented using MATLAB and tested off-line using real respiratory waveform recorded using the stress management system during the subject's breathing exercise.

Figure 15A:
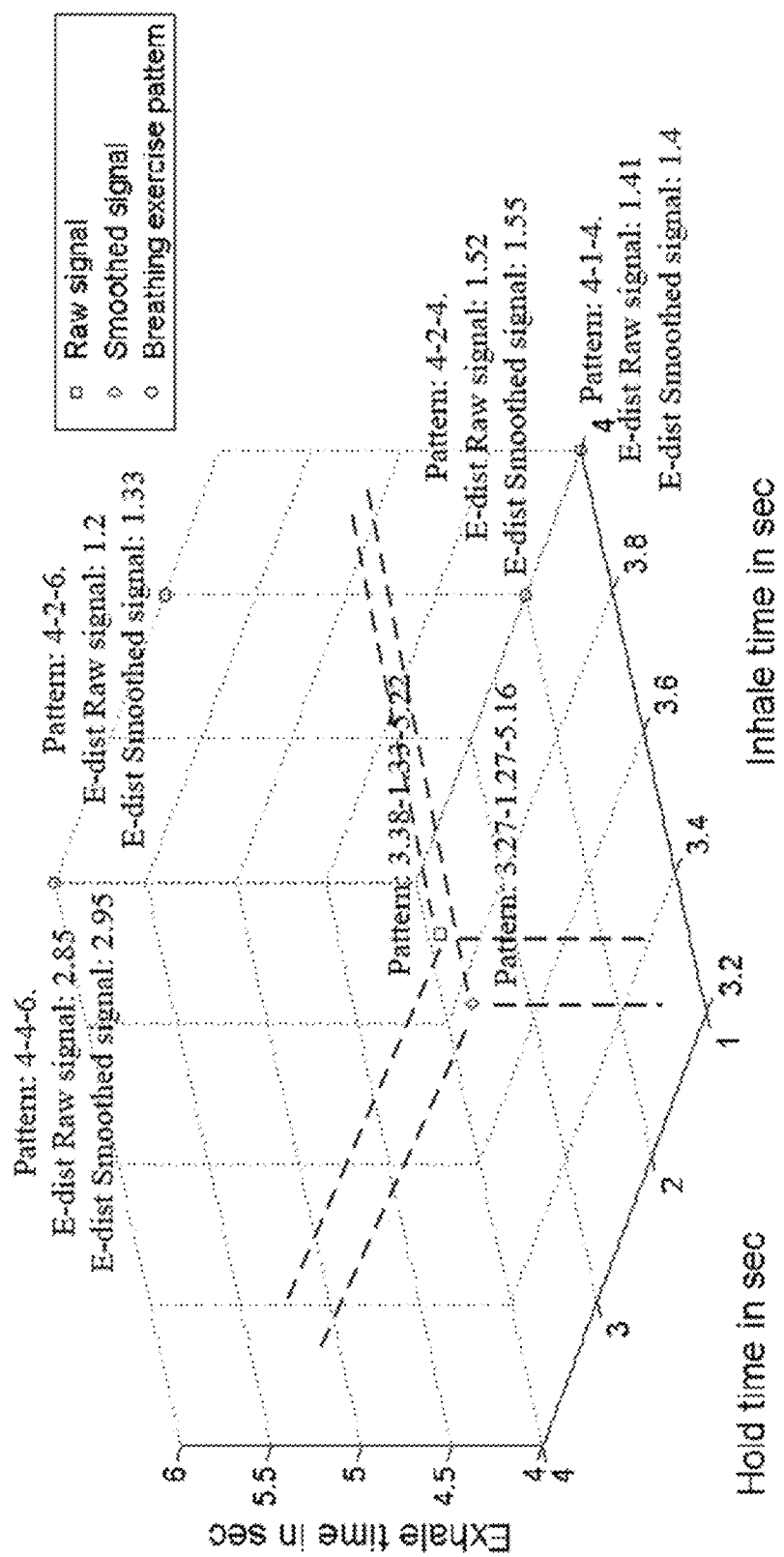

FIG. 15A shows the mapping results and the Euclidean distance ($f_s=18$ Hz). The dashed lines mark the 3D positions of the best fit breathing patterns for the raw respiratory waveform and the smoothed respiratory waveform, respectively. The four trapezoidal breathing patterns are indicated by the circles. Breathing exercise 4-2-6 with a Euclidean distance of 1.2 for the raw respiratory waveform and 1.33 for the smoothed/average waveform were the closest to the average respiratory waveform from both raw respiratory waveform and smoothed/average respiratory waveform.

Figure 15B:
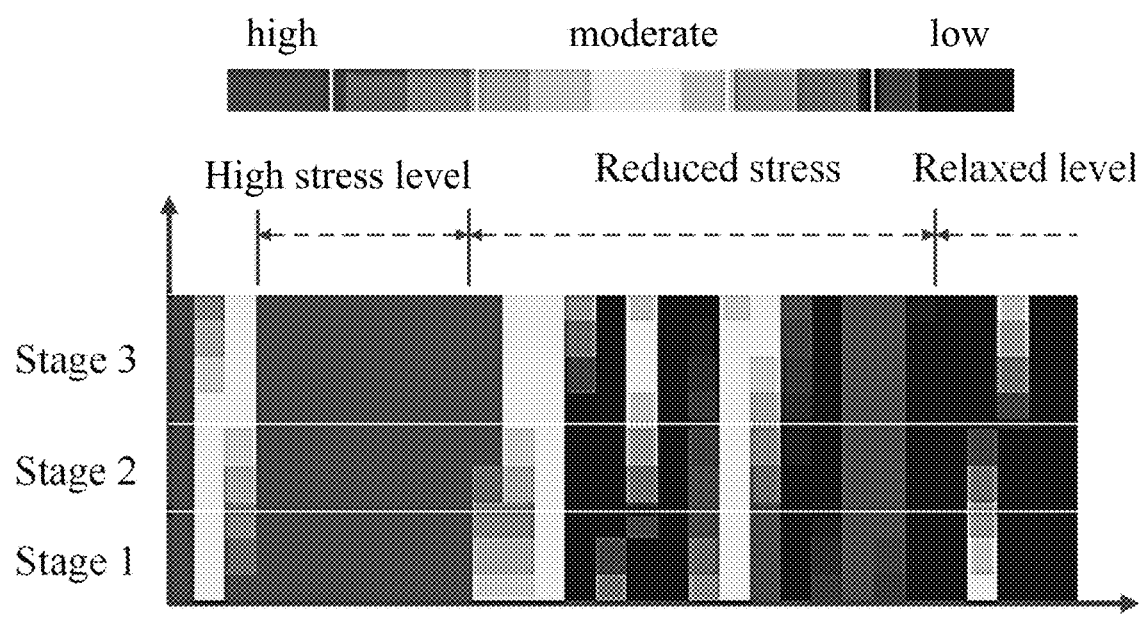
FIG. 15B illustrates an example of a 2D color visualization of stress relief provided by the stress management system of FIGS. 1A and 1B, in accordance with various embodiments of the present disclosure.

In addition, a 2D color visualization can be utilized to provide feedback to the subject by showing the stress change when a test subject is using the stress management system 100. FIG. 15B shows a color map of the stress level changes that can be used to illustrate the changes in the stress levels. The vertical axis is the breathing waveform from stage 1 to stage 3 and the horizontal axis is the time axis where each unit is the time duration of a complete breathing cycle. In the display, a red (or medium grey) color indicates a high stress level and a yellow (or light grey) color indicates a moderate level of stress. A blue (or black) color defines a healthy state with low level stress. These stress levels can be determined from the computed HRV using:

$$\text{color} = \begin{cases} \text{red} & \text{(if } (HRV \le T_{stress})) \\ \text{yellow} & \text{(if } (T_{stress} < HRV \le T_{relaxed})) \\ \text{blue} & \text{(if } (T_{relaxed} < HRV)) \end{cases} \quad (4)$$

$T_{stress}$ and $T_{relaxed}$ are two thresholds which determine the stress level based on HRV. FIG. 15B shows that the test subject is under high level stress during the "High stress level" period on the left side. It can be seen that the red color occupies a large portion on the left side. Then, the stress level starts to decrease around the middle point along the horizontal axis during the "Reduced stress" period where the color map starts to display a mixed color of yellow and blue. Finally, the stress level drops to a healthy level during the "Relaxed level" period. This 2D color visualization can allow users to directly "see" how their stress level changes when they follow the YOGA breathing exercises.

Figure 16A:
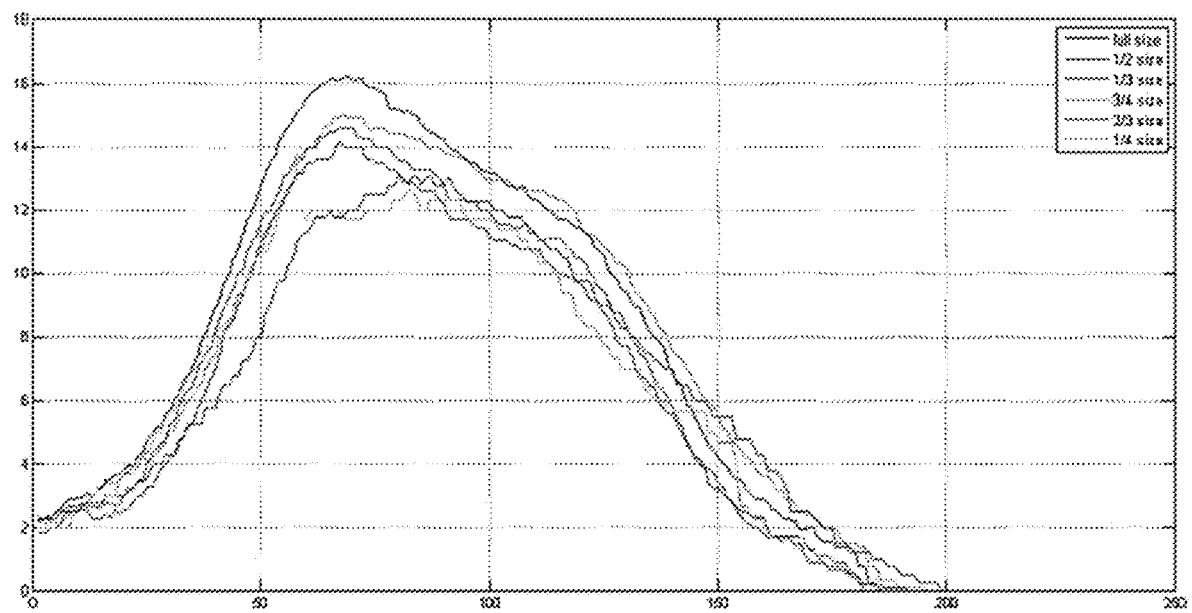
FIGS. 16A through 16C illustrate examples of average respiratory waveforms based upon different amounts (or portions) of raw respiratory waveform, in accordance with various embodiments of the present disclosure.
Figures 16B, 16C:
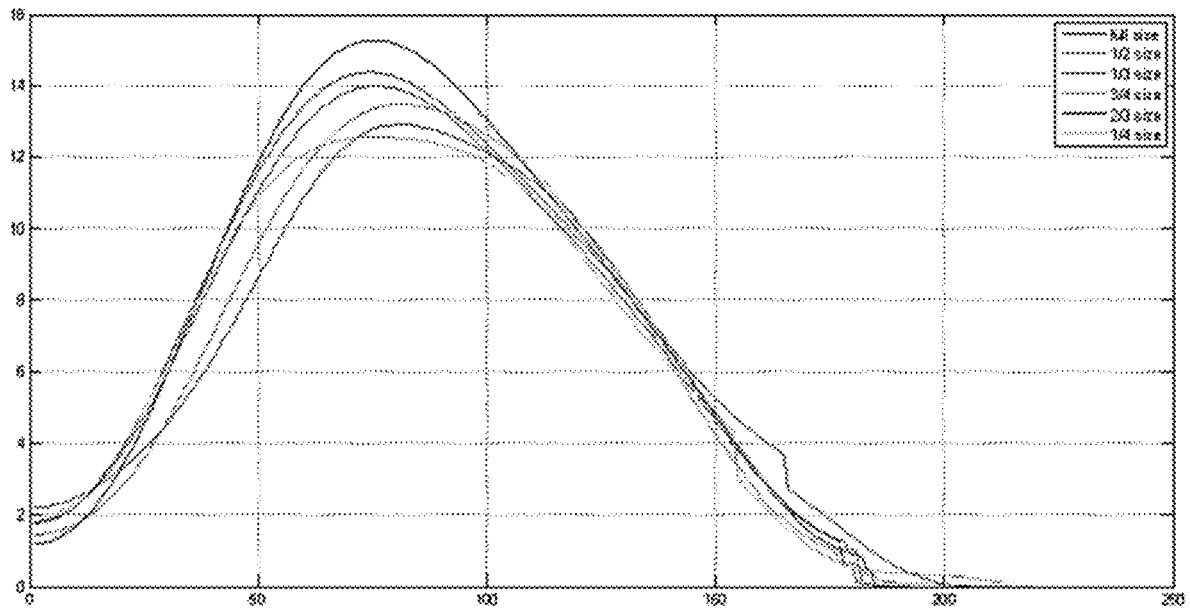

Validation of robustness. Robustness is another criterion that can be used to evaluate the stress management system 100. In order to assess the robustness of the proposed algorithm, the results of the error minimization procedure may be compared using the complete raw respiratory waveform (i.e., the fourteen cycle raw respiratory waveform), ¾ portion of the raw waveform, ⅔ portion, ½ portion, ⅓ portion, and ¼ of raw respiratory waveform. FIG. 16A shows plots of the average respiratory waveform using the different amounts (or portions) of raw respiratory waveform and FIG. 16B shows plots of the average respiratory waveform using the different amounts (or portions) of IFT respiratory waveform.

The robustness assessment may be applied to both the raw respiratory waveform and the IFT-processed respiratory waveforms. The table in FIG. 16C shows the outcome of this assessment. From the table, it can be seen that results from the raw respiratory waveform match well with the ones from the IFT-processed respiratory waveform. This shows that the IFT-processed respiratory waveform can capture the essence of the raw respiratory waveform well. Only the smoothed respiratory waveform may be used to find the valleys to then superimpose and average the so-identified respective raw respiratory waveform data rather than the IFT-processed respiratory waveform data of each individual breathing cycle in order to not introduce additional artifacts when performing the best trapezoidal fit. However, in another instantiation, the best trapezoidal fit can also be performed on the IFT-processed respiratory waveform data. Vertically comparing the results ($x_1$, $x_2$, $x_3$, and $x_4$) in the table of FIG. 16C with different amounts of data (i.e., different number of breathing cycles) also indicates that the amount of data has no significant influence on the optimization results. Therefore, the proposed algorithm appears to be robust.

Root Mean Square Error (RMSE) for Heartbeat Motif Identification. Other waveform identification can also be implemented by the stress management system 100. For example, a pattern or motif in a stream of data/signals in the presence of noise, either in real- or near real-time, or via post-processing. Root Mean Square Error (RMSE) or related measures, such as the Hamming Distance, measure the exact difference between two time series of the same length. Given two time series A={$a_1$, . . . , $a_n$} and B={$b_1$, . . . , $b_n$}, the root mean square error can be computed as:

$$RMSE(A, B) = \sqrt{\frac{1}{n}\left(\sum_{i=1}^{N-1}(a_i - b_i)^2\right)} \quad (5)$$

Equation (5) can be used to identify whether two time series are vastly different or very similar, or in general the degree of similarity. For example, if there is a low RMSE using equation (5), then it can be concluded that the two time series A and B are similar. In the application example of HRV determination, the similarity of heartbeat patterns is considered. These heartbeat patterns can be referred to as a "motif". Motifs can be associated with different diseases or heart conditions, or with emotional stages. For example, different heartbeat motifs can be used as a set of templates that can be used to try to find all measured or incoming (e.g., from a wearable sensor) ECG waveforms that correspond to the respective motifs and mark them as such. ECG waveforms that are not identified as belonging to the known motifs, may be marked as artifacts for subsequent removal, and/or may give rise to the detection of a previously unencountered motif.

For instance, some of the raw ECG data can be used as training data to extract a motif typical for a breathing exercise or a body exercise (e.g., pushups, resting, etc.). Either the user determines the time-length of such a motif and uses one raw heartbeat waveform directly as the motif, or, several raw heartbeat cycles can be averaged to result in a more robust formulation or definition of the motif. In yet another embodiment, a motif is generated automatically, i.e., without a user's help, e.g., by using machine learning techniques. This training can be repeated for other activities to produce a library of well-established motifs. The library of established heartbeat motifs can then be used to identify patterns in real-time, near real-time or may be used in an off-line, post-processing mode.

By running them across (e.g., by window-shifting) an incoming stream of raw ECG waveform data (e.g., from a wearable sensor 103), the resulting RMSE can be calculated at each time-step across the time-window-width of the respective motif. This RMSE value can be plotted for evaluation against the time-step. For example, using the logarithm of the RMSE that was calculated, the onset of the respective identified motifs can more easily be identified in the raw ECG waveform data (e.g., through non-linear enhancement). The onset of a successfully identified motif will be denoted by a sharp and steep minimum in the semi-logarithmic plot of the RMSE over time (i.e., logarithm of RMSE plotted as a function of time as in FIG. 17B). The resulting time differences between these minima are good/accurate estimations of the RR intervals, from which, in one instantiation, the HRV can be calculated.

Figure 17A:
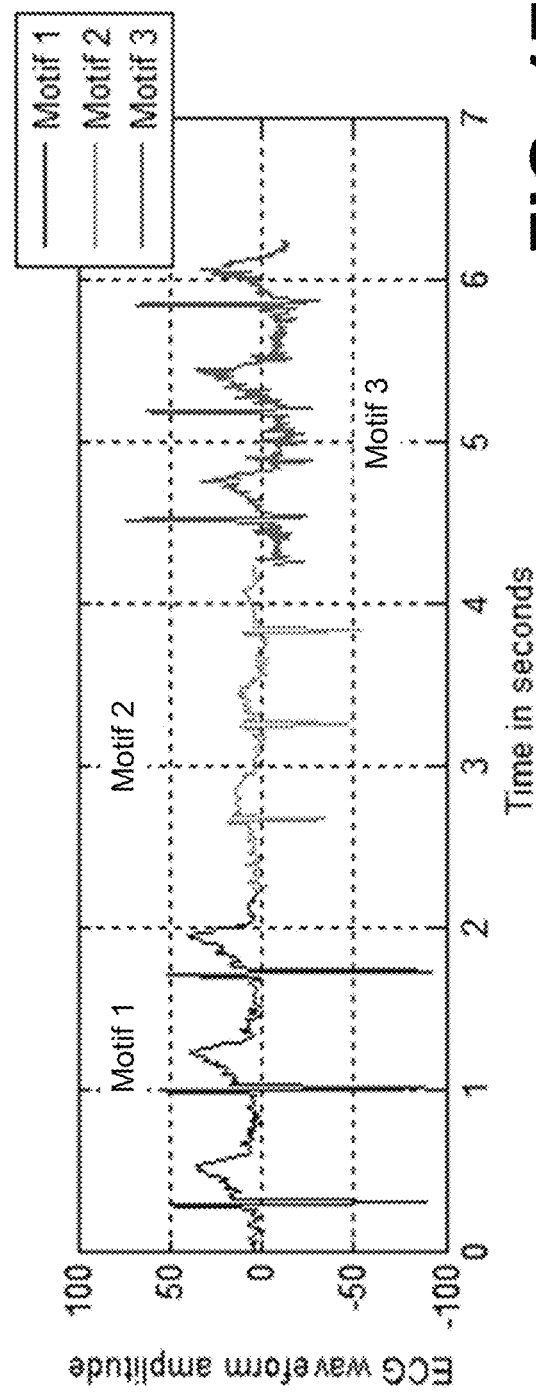
FIGS. 17A and 17B illustrate an example of the evaluation of waveforms of the data in FIG. 9 based upon RMSE, in accordance with various embodiments of the present disclosure.
Figure 17B:
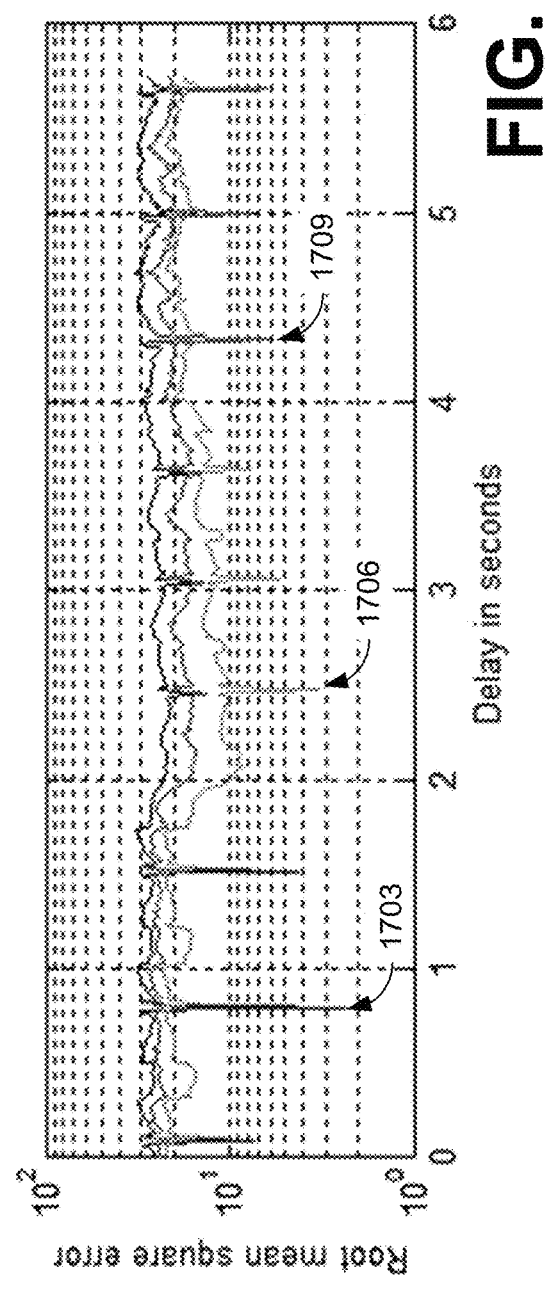

FIGS. 17A and 17B show examples of RMSE calculation results from a set of nine recorded raw ECG waveforms and the resulting motif identification. FIG. 17A displays the identification of three different heartbeat motifs among the nine raw ECG waveforms. Here, the horizontal axis represents the time in seconds and the vertical axis is the ECG waveform amplitude. FIG. 17B shows the resulting RMSE that was calculated according to equation (5) when window-shifting each of the three heartbeat motifs/templates along the time axis (i.e., x-axis) across the nine consecutive raw ECG waveforms. Again, the horizontal axis is the time stamp of the raw ECG waveforms and the vertical axis is the logarithm of the RMSE value.

Plot 1703 shows the RMSE results using the first heartbeat motif (Motif 1). Plots 1706 and 1709 correspond to the RMSE results using the second and third heartbeat motifs, Motif 2 and Motif 3 respectively. During the first two seconds, the RMSE of the first heartbeat motif (Motif 1) produces three local minima corresponding to the onsets of the first three heartbeats in FIG. 17A. This indicates that the first three raw ECG waveforms correspond to or are most similar to heartbeat motif 1 (1703). The RMSE for the second and third heartbeat motifs also generate local minima in the same way starting at 2.2 seconds and 4.2 seconds, respectively. The time differences between these local minima are good/accurate estimations for the RR peak intervals of the raw ECG waveforms. The experimental results indicate that the RMSE-based method can effectively identify different heartbeat motifs and extract RR peak intervals from raw ECG waveforms coming, e.g., from a wearable sensor 103.

Enhanced Motif Identification through Optimization. The data, e.g., coming from wearable sensor technologies 103, can be noisy. As such, the time-window-width of predetermined motifs may have to be relaxed and may not be fixed. For example, while the overall shape of a raw ECG waveform may correspond to a pre-selected motif, its time-window-width may be compressed or stretched/enlarged compared to the pristine motif. To still enable reliable recognition/identification of motifs in raw ECG waveform data streams, an optimization may need to be engaged (e.g., using a framework such as the "*Stochastic Optimization Framework*" by W. Fink (Proc. SPIE, Vol. 6960, 69600N, 2008) that compresses or stretches a pristine motif within a reasonable range before running it across the raw ECG data to minimize the overall resulting RMSE across the time interval of the entire raw ECG data (e.g., minimize the integral of the RMSE curve across the entire data time interval).

The notion of a Motif is not limited to a heartbeat pattern as described above. The notion of a motif can comprise a diverse set of things, such as, but not limited to: a land/sea-mine signature, a star signature (e.g., pulsar), a tracking and/or reflection signature of a particular orbital debris for space situational awareness tasks, a signature in the stock market (e.g., formations within a course chart of a particular stock), hyperspectral signature of an object, e.g., explosives or rocket plumes, etc. The data provided in any of these situations can be analyzed using learned, generated or defined motifs as has been discussed.

Figure 18:
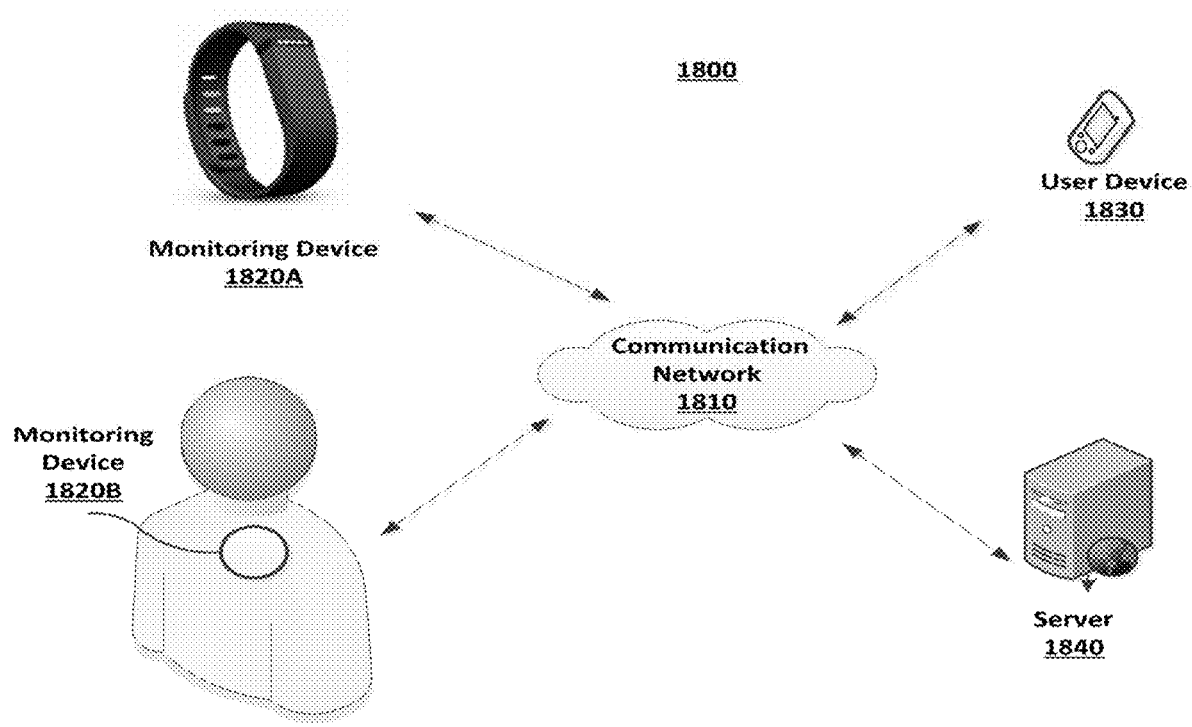
FIG. 18 is an example of a network environment of the stress management system of FIGS. 1A and 1B, in accordance with various embodiments of the present disclosure.

FIG. 18 illustrates a network environment 1800 in which a system for processing respiratory data (e.g., the stress management system 100) may be implemented. Network environment 1800 may include a communication network 1810, one or more monitoring devices 1820A-B, a user device 1830, and an optional server 1840. Devices in network environment 1800 may communicate with each other via communications network 1810. The communication network 1810 may be a local, proprietary network (e.g., an intranet) and/or may be a part of a larger wide-area network. The communications network 1810 may be a local area network (LAN), which may be communicatively coupled to a wide area network (WAN) such as the Internet. The Internet is a broad network of interconnected computers and servers allowing for the transmission and exchange of Internet Protocol (IP) data between users connected through a network service provider. Examples of network service providers are the public switched telephone network, a cable service provider, a provider of digital subscriber line (DSL) services, or a satellite service provider. Communications network 1810 allows for communication between the various components of network environment 1800.

Monitoring devices 1820A-B may include any type of monitoring device known in the art (e.g., an Apple Watch, Fitbit, etc.). Monitoring device 1820 may include one or more sensors, which may or may not be incorporated into a wearable device. Such sensors may include impedance pneumograph sensors, electrocardiograph (ECG) sensors that detect and measure electrical activity in the heart of a person when placed in proximity thereto (e.g., against the skin on the chest of the person), and other biometric sensors. Another type of sensor that may be included in monitor devices is an actigraph sensor for detecting movement. Such an actigraph sensor may be capable, for example, of detecting and measuring the movement of the chest of a person. Such movements may be indicative of the breathing (e.g., rate, depth) of the person. Similarly, an accelerometer sensor may be included in monitor devices. Any other type of medical and health-related biosensors known in the art may also be included in monitoring device 1820. In this regard, monitoring device 1820 may be able to gather data regarding respiration, posture, intraocular pressure, blood sugar level, blood oxygenation level, activity level of the person, and other biodata of the person. Other types of sensors may include radar, sonar, and lidar.

Users may use any number of different electronic user devices 1830, such as general purpose computers, mobile phones, smartphones, personal digital assistants (PDAs), portable computing devices (e.g., laptop, netbook, tablets), desktop computing devices, handheld computing device, or any other type of computing device capable of communicating over communication network 1810. User devices 1830 may also be configured to access data from other storage media, such as memory cards or disk drives as may be appropriate in the case of downloaded services. User device 1830 may include standard hardware computing components such as network and media interfaces, non-transitory computer-readable storage (memory), and processors for executing instructions that may be stored in memory.

Server 1840 may include any type of server or other computing device as is known in the art, including standard hardware computing components such as network and media interfaces, non-transitory computer-readable storage (memory), and processors for executing instructions or accessing information that may be stored in memory. The functionalities of multiple servers may be integrated into a single server. Any of the aforementioned servers (or an integrated server) may take on certain client-side, cache, or proxy server characteristics. These characteristics may depend on the particular network placement of the server or certain configurations of the server. The server 1840 may be inclusive of one or more cloud servers, which can be collocated or in different locations. Processing may occur solely on the user device 1830, solely on the server 1840 (or cloud server), or split among multiple devices.

Figure 19:
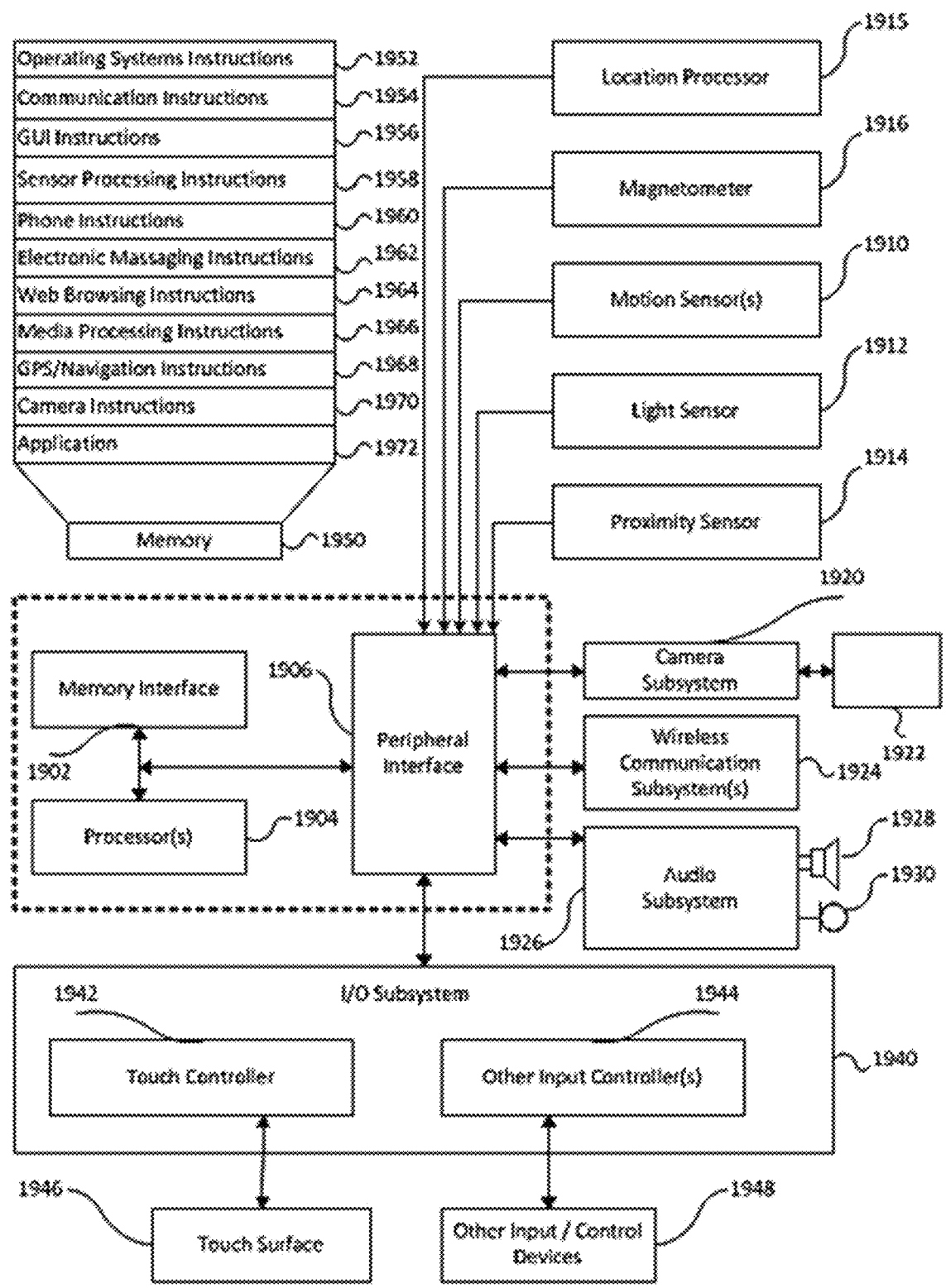
FIG. 19 is an example of a computing device or mobile platform architecture, in accordance with various embodiments of the present disclosure.

FIG. 19 illustrates a computing device architecture (e.g., a mobile platform, server, etc.) that may be utilized to implement the various features and processes described herein. Architecture 1900 can be implemented in any number of computing devices including but not limited to monitoring devices (e.g., monitoring devices 1820A-B) and user devices (e.g., user device 1830), which may include smartphones, tablets, or other computing device known in the art. Architecture 1900 as illustrated in FIG. 19 includes memory interface 1902, processors 1904, and peripheral interface 1906. Memory interface 1902, processors 1904 and peripherals interface 1906 can be separate components or can be integrated as a part of one or more integrated circuits. The various components can be coupled by one or more communication buses or signal lines.

Processors 1904 as illustrated in FIG. 19 is meant to be inclusive of data processors, image processors, central processing unit, or any variety of multi-core processing devices. Any variety of sensors, external devices, and external subsystems can be coupled to peripherals interface 1906 to facilitate any number of functionalities within the architecture 1900 of the exemplar mobile device. For example, motion sensor 1910, light sensor 1912, and proximity sensor 1914 can be coupled to peripherals interface 1906 to facilitate orientation, lighting, and proximity functions of the mobile device. For example, light sensor 1912 could be utilized to facilitate adjusting the brightness of touch surface 1946. Motion sensor 1910, which could be exemplified in the context of an accelerometer or gyroscope, could be utilized to detect movement and orientation of the mobile device. Display objects or media could then be presented according to a detected orientation (e.g., portrait or landscape).

Other sensors could be coupled to peripherals interface 1906, such as a temperature sensor, a biometric sensor, blood sugar sensor, blood oxygenation sensor, or other sensing device to facilitate corresponding functionalities. In some embodiments, the sensors can include lidar, sonar, and/or radar. Location processor 1915 (e.g., a global positioning transceiver) can be coupled to peripherals interface 1906 to allow for generation of geo-location data thereby facilitating geo-positioning. An electronic magnetometer 1916 such as an integrated circuit chip could in turn be connected to peripherals interface 1906 to provide data related to the direction of true magnetic North whereby the mobile device could enjoy compass or directional functionality. Camera subsystem 1920 and an optical sensor 1922 such as a charged coupled device (CCD) or a complementary metal-oxide semiconductor (CMOS) optical sensor can facilitate camera functions such as recording photographs and video clips.

Communication functionality can be facilitated through one or more communication subsystems 1924, which may include one or more wireless communication subsystems. Wireless communication subsystems 1924 can include 802.x or Bluetooth transceivers as well as optical transceivers such as infrared. Wired communication system can include a port device such as a Universal Serial Bus (USB) port or some other wired port connection that can be used to establish a wired coupling to other computing devices such as network access devices, personal computers, printers, displays, or other processing devices capable of receiving or transmitting data. The specific design and implementation of communication subsystem 1924 may depend on the communication network or medium over which the device is intended to operate. For example, a device may include wireless communication subsystem designed to operate over a global system for mobile communications (GSM) network, a GPRS network, an enhanced data GSM environment (EDGE) network, 802.x communication networks, code division multiple access (CDMA) networks, or Bluetooth networks. Communication subsystem 1924 may include hosting protocols such that the device may be configured as a base station for other wireless devices. Communication subsystems can also allow the device to synchronize with a host device using one or more protocols such as TCP/IP, HTTP, or UDP.

Audio subsystem 1926 can be coupled to a speaker 1928 and one or more microphones 1930 to facilitate voice-enabled functions. These functions might include voice recognition, voice replication, or digital recording. Audio subsystem 1926 in conjunction may also encompass traditional telephony functions.

I/O subsystem 1940 may include touch controller 1942 and/or other input controller(s) 1944. Touch controller 1942 can be coupled to a touch surface 1946. Touch surface 1946 and touch controller 1942 may detect contact and movement or break thereof using any of a number of touch sensitivity technologies, including but not limited to capacitive, resistive, infrared, or surface acoustic wave technologies. Other proximity sensor arrays or elements for determining one or more points of contact with touch surface 1946 may likewise be utilized. In one implementation, touch surface 1946 can display virtual or soft buttons and a virtual keyboard, which can be used as an input/output device by the user.

Other input controllers 1944 can be coupled to other input/control devices 1948 such as one or more buttons, rocker switches, thumb-wheels, infrared ports, USB ports, and/or a pointer device such as a stylus. The one or more buttons (not shown) can include an up/down button for volume control of speaker 1928 and/or microphone 1930. In some implementations, device 1900 can include the functionality of an audio and/or video playback or recording device and may include a pin connector for tethering to other devices.

Memory interface 1902 can be coupled to memory 1950. Memory 1950 can include high-speed random access memory or non-volatile memory such as magnetic disk storage devices, optical storage devices, or flash memory. Memory 1950 can store operating system 1952, such as Darwin, RTXC, LINUX, UNIX, OS X, ANDROID, WINDOWS, or an embedded operating system such as, e.g., VxWorks. Operating system 1952 may include instructions for handling basic system services and for performing hardware dependent tasks. In some implementations, operating system 1952 can include a kernel.

Memory 1950 may also store communication instructions 1954 to facilitate communicating with other mobile computing devices or servers. Communication instructions 1954 can also be used to select an operational mode or communication medium for use by the device based on a geographic location, which could be obtained by the GPS/Navigation instructions 1968. Memory 1950 may include graphical user interface instructions 1956 to facilitate graphic user interface processing such as the generation of an interface; sensor processing instructions 1958 to facilitate sensor-related processing and functions; phone instructions 1960 to facilitate phone-related processes and functions; electronic messaging instructions 1962 to facilitate electronic-messaging related processes and functions; web browsing instructions 1964 to facilitate web browsing-related processes and functions; media processing instructions 1966 to facilitate media processing-related processes and functions; GPS/Navigation instructions 1968 to facilitate GPS and navigation-related processes, camera instructions 1970 to facilitate camera-related processes and functions; and instructions 1972 for any other application that may be operating on or in conjunction with the mobile computing device.

Memory 1950 may also store other software instructions for facilitating other processes, features and applications, such as applications related to navigation, social networking, location-based services or map displays. Each of the above identified instructions and applications can correspond to a set of instructions for performing one or more functions described above. These instructions need not be implemented as separate software programs, procedures, or modules. Memory 1950 can include additional or fewer instructions. Furthermore, various functions of the mobile device may be implemented in hardware and/or in software, including in one or more signal processing and/or application specific integrated circuits.

Embodiments of the present invention may be implemented in an application that may be operable using a variety of devices. Non-transitory computer-readable storage media refer to any medium or media that participate in providing instructions to a central processing unit (CPU) for execution. Such media can take many forms, including, but not limited to, non-volatile and volatile media such as optical or magnetic disks and dynamic memory, respectively. Common forms of non-transitory computer-readable media include, for example, a floppy disk, a flexible disk, a hard disk, magnetic tape, any other magnetic medium, a CD-ROM disk, digital video disk (DVD), any other optical medium, RAM, PROM, EPROM, a FLASHEPROM, and any other memory chip or cartridge.

Various forms of transmission media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU. Various forms of storage may likewise be implemented as well as the necessary network interfaces and network topologies to implement the same.

As disclosed above, embodiments of the present disclosure are related to signal processing, and can allow for real-time (or near real-time) analysis of waveforms included in received data. Patterns or motifs can be identified in a stream of data and/or signals and used to initiate or control responses and/or interventions. In one embodiment, among others, a method for processing data to select a pattern comprises receiving data via one or more sensors; executing instructions stored in memory to determine the selected pattern; and generating a notification regarding the selected pattern. Execution of the instructions by a processor evaluates the received data over a time domain, where the received data evaluated over the time domain comprises waveforms; averages the waveforms to obtain a mean waveform; and selects the pattern based on the mean waveform. In one embodiment, among others, the pattern can comprise a start time, a hold time, and an end time. In one or more aspects of these embodiments, the data can comprise at least one of respiratory data, intraocular pressure data, radar data, sonar data, or lidar data. The one or more sensors can be part of a wearable device. The pattern can be a breathing pattern. At least some of the data can be received by or from the one or more sensors in real-time. At least some of the data can be evaluated over the time domain in real-time.

In one or more aspects of these embodiments, the method can comprise identifying one or more peaks and/or valleys in the waveforms, wherein a space between two consecutive valleys represents a cycle. In other embodiments, other markers or formations in the data can be identified. The method can comprise processing each waveform to remove effects of noise and defects. Processing the waveform can comprise identifying one or more significant coefficients in a frequency domain, and removing any coefficients that are not identified as significant in the frequency domain. Removing the coefficients not identified as significant can result in a smoothed waveform. In one or more aspects of these embodiments, the method can comprise identifying one or more peaks and/or valleys in the smoothed waveforms. A space between two consecutive valleys can represent a cycle. The sensors can include at least one of an impedance pneumograph sensor, intraocular pressure sensor, blood sugar sensor, blood oxygenation sensor, radar, sonar, or lidar. The notification can be displayed on a display screen. The notification can include an auditory message, a text message, or a posting on a website (e.g., a social media website).

In another embodiment, a system for processing data to select a pattern comprises one or more sensors, where each sensor detects data; a processor that executes instructions stored in memory to determine the selected pattern; and a user interface that communicates a notification regarding the selected pattern. Execution of the instructions by the processor evaluates the received data over a time domain, where the received data evaluated over the time domain comprises waveforms; averages the waveforms to obtain a mean waveform; and selects a pattern based on the mean waveform. The pattern can comprise a start time, a hold time, and an end time. In one or more aspects of these embodiments, the data can comprise at least one of respiratory data, intraocular pressure data, blood sugar sensor, blood oxygenation sensor, radar data, sonar data, or lidar data. The one or more sensors can be part of a wearable device. The pattern can be a breathing pattern. The one or more sensors can detect at least some of the data in real-time.

In one or more aspects of these embodiments, the processor can evaluate at least some of the received data over the time domain in real-time. The processor can execute instructions to identify one or more peaks and/or valleys in the waveforms. A space between two consecutive valleys can represent a cycle. In other embodiments, other markers or formations in the data can be identified. The processor can execute instructions to process each waveform to remove effects of noise and defects. In one or more aspects of these embodiments, processing the waveform can comprise identifying one or more significant coefficients in a frequency domain, and removing any coefficients that are not identified as significant in the frequency domain. Removing the coefficients not identified as significant can result in a smoothed waveform. The processor can execute instructions to identify one or more peaks and/or valleys in the smoothed waveforms. A space between two consecutive valleys can represent a cycle. In other embodiments, other markers or formations in the data can be identified. The sensors can include at least one of an impedance pneumograph sensor, intraocular pressure sensor, blood sugar sensor, blood oxygenation sensor, radar, sonar, or lidar. The processor can be at a user device remote from the one or more sensors, and the one or more sensors can provide the data to the user device via a wireless communication network. The system can comprise a display screen that displays the notification. The notification can include an auditory message, and the system can comprise a speaker that plays the auditory message. In other embodiments, the notification can include a text message or a posting on a website (e.g., a social media website).

In another embodiment, a non-transitory computer-readable storage medium has embodied thereon a program executable by a processor to perform a method for processing data to select a pattern. The method comprises receiving data via one or more sensors; evaluating the received data over a time domain, where the received data evaluated over the time domain comprises waveforms; averaging the waveforms to obtain a mean waveform; selecting a pattern based on the mean waveform, wherein the pattern comprises a start time, a hold time, and an end time; and generating a notification regarding the selected pattern. In one or more aspects of these embodiments, at least some of the received data can be received in real-time. At least some of the received data can be evaluated over a time domain in real-time.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

The invention claimed is:

1. A method for managing stress of a subject based on a selected pattern, the method comprising:
receiving data via one or more sensors used for monitoring a stress level of a subject, the one or more sensors wearable by the subject;
executing instructions stored in memory by processing circuitry comprising a processor, where execution of the instructions-by the processing circuitry:
evaluates at least a portion of the received data over a time domain, where the portion of the received data evaluated over the time domain comprises a plurality of respiratory waveforms, each of the plurality of respiratory waveforms associated with a different cycle of the received data,
averages the plurality of respiratory waveforms to generate a mean waveform in the time domain, and
selects a time domain pattern based on an error comparison with the mean waveform, where the selected time domain pattern is a breathing pattern for the subject that comprises a start time, a hold time, and an end time; and
generating a stress notification regarding the selected time domain pattern, the stress notification comprising feedback prompting respiration modification of the subject to adjust the monitored stress level of the subject, and in response to a detected change in the monitored stress level based on subsequent data received via the one or more sensors, generating real-time or near real-time feedback regarding effect of modification of the monitored stress level of the subject, the feedback comprising an indication of the detected change in the monitored stress level.

2. The method of claim 1, wherein the one or more sensors include at least one of an electrocardiogram sensor, a respiratory sensor, an actigraph sensor, an accelerometer, a gyroscope, an impedance pneumograph sensor, an intraocular pressure sensor, a blood sugar sensor, a blood oxygenation sensor, or a temperature sensor.

3. The method of claim 1, wherein the one or more sensors are part of a wearable device worn by the subject.

4. The method of claim 1, wherein the portion of the received data is evaluated over the time domain in real-time.

5. The method of claim 1, further comprising identifying one or more peaks or valleys in the plurality of respiratory waveforms, wherein a space between two consecutive valleys represents a cycle.

6. The method of claim 1, further comprising processing each respiratory waveform of the plurality of respiratory waveforms to remove effects of noise and defects.

7. The method of claim 6, wherein processing each respiratory waveform of the plurality of respiratory waveforms comprises:
identifying one or more significant coefficients in a frequency domain, and
removing any coefficients that are not identified as significant in the frequency domain, wherein removing the coefficients not identified as significant results in a smoothed waveform.

8. The method of claim 7, further comprising identifying one or more peaks and valleys in the smoothed waveforms, wherein a space between two consecutive valleys represents a cycle.

9. A system for managing stress of a subject based on a selected pattern, the system comprising:
one or more sensors wearable by a subject, where each sensor detects data associated with a monitored stress level of the subject, the data transmitted to a mobile platform in real-time;

the mobile platform comprising a processor that executes instructions stored in memory, where execution of the instructions by the processor:
- evaluates at least a portion of the data over a time domain, where the portion of the data evaluated over the time domain comprises a plurality of respiratory waveforms, each of the plurality of respiratory waveforms associated with a different cycle of the received data,
- averages the plurality of respiratory waveforms to generate a mean waveform in the time domain, and
- selects a time domain pattern based on an error comparison with the mean waveform, where the selected time domain pattern is a breathing pattern for the subject that comprises a start time, a hold time, and an end time; and a user interface that communicates a stress notification regarding the selected time domain pattern, the stress notification comprising feedback prompting respiratory modification of the subject to adjust the monitored stress level of the subject, and in response to a detected change in the monitored stress level based on subsequent data received via the one or more sensors, generating real-time or near real-time feedback regarding effect of modification of the monitored stress level of the subject, the feedback comprising an indication of the detected change in the monitored stress level.

10. The system of claim 9, wherein the one or more sensors are part of a wearable device configured for use by the subject.

11. The system of claim 10, wherein the data from the one or more sensors are transmitted to the mobile platform from the wearable device via a wireless communication link.

12. The system of claim 9, wherein the one or more sensors include at least one of an electrocardiogram sensor, a respiratory sensor, an actigraph sensor, an accelerometer, a gyroscope, an impedance pneumograph sensor, intraocular pressure sensor, blood sugar sensor, blood oxygenation sensor, or temperature sensor.

13. The system of claim 9, wherein the processor executes instructions to identify one or more peaks or valleys in the plurality of respiratory waveforms, wherein a space between two consecutive valleys represents a cycle.

14. The system of claim 13, wherein the one or more peaks or valleys are identified based upon Root Mean Square Error (RMSE) analysis of the plurality of respiratory waveforms.

15. The system of claim 9, wherein the processor executes instructions to process each respiratory waveform of the plurality of respiratory waveforms to remove effects of noise and defects.

16. The system of claim 15, wherein processing each respiratory waveform of the plurality of respiratory waveforms comprises:
- identifying one or more significant coefficients in a frequency domain, and
- removing any coefficients that are not identified as significant in the frequency domain, wherein removing the coefficients not identified as significant results in a smoothed waveform.

17. The system of claim 9, wherein the mobile platform is remote from the one or more sensors, and at least the portion of the data from the one or more sensors is provided to the mobile platform via a wireless communication link.

18. The system of claim 9, wherein the stress notification is provided graphically via a display screen of the mobile platform or audibly via a speaker of the mobile platform.

19. The method of claim 1, the method further comprising:
- generating a characteristic of at least one pattern based at least in part upon an onset of at least one defined motif;
- wherein execution of the instructions by the processing circuitry comprising the processor:
  - compares window-shifted segments of the received data to the at least one defined motif, and
  - determines the onset of the at least one defined motif in the received data based upon the comparison.

20. The method of claim 19, wherein the at least one motif corresponds to a specified condition associated with the received data.

21. The method of claim 20, wherein the onset of the at least one motif is determined based upon a logarithm of a Root Mean Square Error (RMSE) between the at least one defined motif and the window-shifted segments of the received data.

22. The system of claim 9, wherein operation of a breathing apparatus is controlled via the feedback.

23. The method of claim 1, wherein operation of a breathing apparatus is controlled via the feedback.

* * * * *